United States Patent
Kellar et al.

(10) Patent No.: US 7,905,919 B2
(45) Date of Patent: Mar. 15, 2011

(54) PROSTHETIC JOINT

(75) Inventors: Franz W. Kellar, Gastonia, NC (US); Harold Lloyd Crowder, Concord, NC (US)

(73) Assignee: BioMedFlex LLC, Gastonia, NC (US)

( * ) Notice: Subject to any disclaimer, the term of this patent is extended or adjusted under 35 U.S.C. 154(b) by 0 days.

(21) Appl. No.: 12/714,288

(22) Filed: Feb. 26, 2010

(65) Prior Publication Data

US 2010/0280623 A9    Nov. 4, 2010

Related U.S. Application Data

(63) Continuation-in-part of application No. 11/936,601, filed on Nov. 7, 2007.

(60) Provisional application No. 60/864,667, filed on Nov. 7, 2006.

(51) Int. Cl.
*A61F 2/28* (2006.01)
*A61F 2/44* (2006.01)
*A61F 2/30* (2006.01)
*A61F 2/32* (2006.01)

(52) U.S. Cl. ............... 623/16.11; 623/17.14; 623/18.11; 623/22.11; 623/22.3; 623/23.4; 623/23.43

(58) Field of Classification Search ............... 623/16.11, 623/17.11–17.16, 18.11, 19.11–19.13, 20.14–20.15, 623/20.21–20.24, 20.28–20.33, 20.35, 21.13, 623/21.16–21.18, 22.11, 22.13–22.19, 22.21–22.23, 623/22.24–22.3, 23.39–23.41, 23.43

See application file for complete search history.

(56) References Cited

U.S. PATENT DOCUMENTS

| 3,723,995 | A |   | 4/1973 | Baumann |
|---|---|---|---|---|
| 3,744,061 | A |   | 7/1973 | Frost |
| 4,031,570 | A |   | 6/1977 | Frey |
| 4,159,544 | A | * | 7/1979 | Termanini ............... 623/22.14 |

(Continued)

FOREIGN PATENT DOCUMENTS

GB    1528906    10/1978

(Continued)

OTHER PUBLICATIONS

Wenzel, S.A. and Shepherd, D.E.T., "Contact Stresses in Lumbar Total Disc Arthroplasty", vol. 17, No. 3, 2007, pp. 169-173, "Biomedical Materials and Engineering", Edgbaston, UK.

(Continued)

*Primary Examiner* — David Isabella
*Assistant Examiner* — Andrew Iwamaye
(74) *Attorney, Agent, or Firm* — Trego, Hines & Ladenheim, PLLC

(57) ABSTRACT

A prosthetic joint includes: (a) a bone-implantable first member comprising a rigid material and including a body having an annular flange extending outward at a first end thereof, the first end of the body and the flange cooperatively defining a wear-resistant concave first contact surface having a protruding rim and a recessed central portion; and (b) a bone-implantable second member comprising a rigid material with a wear-resistant convex second contact surface; (c) where the first and second contact surfaces bear directly against each other so as to transfer axial and lateral loads from one of the members to the other, while allowing pivoting motion between the two members; (d) wherein the flange is shaped so as to deform elastically and permit the first contact surface to conform to the second contact surface when the joint is placed under a predetermined load.

11 Claims, 19 Drawing Sheets

U.S. PATENT DOCUMENTS

| | | |
|---|---|---|
| 4,550,450 A | 11/1985 | Kinnett |
| 4,759,766 A | 7/1988 | Buettner-Janz et al. |
| 4,813,961 A * | 3/1989 | Sostegni ................... 623/23.39 |
| 4,955,919 A | 9/1990 | Pappas et al. |
| 4,997,432 A | 3/1991 | Keller |
| 5,062,853 A * | 11/1991 | Forte ............................ 623/22.2 |
| 5,080,678 A | 1/1992 | Spotorno et al. |
| 5,092,898 A | 3/1992 | Bekki et al. |
| 5,181,926 A | 1/1993 | Koch et al. |
| 5,197,987 A | 3/1993 | Koch et al. |
| 5,462,362 A | 10/1995 | Yuhta et al. |
| 5,480,442 A | 1/1996 | Bertagnoli |
| 5,507,816 A | 4/1996 | Bullivant |
| 5,549,693 A * | 8/1996 | Roux et al. ................. 623/22.14 |
| 5,549,699 A | 8/1996 | MacMahon et al. |
| 5,549,700 A * | 8/1996 | Graham et al. ............ 623/22.14 |
| 5,593,445 A | 1/1997 | Waits |
| 5,674,296 A | 10/1997 | Bryan et al. |
| 5,676,701 A | 10/1997 | Yuan et al. |
| 5,702,470 A | 12/1997 | Menon |
| 5,879,406 A | 3/1999 | Lilley |
| 5,893,889 A | 4/1999 | Harrington |
| 5,916,269 A | 6/1999 | Serbousek et al. |
| 5,957,979 A | 9/1999 | Beckman et al. |
| 5,989,294 A | 11/1999 | Marlow |
| 6,059,830 A | 5/2000 | Lippincott, III et al. |
| 6,096,083 A * | 8/2000 | Keller et al. ............... 623/22.11 |
| 6,126,695 A | 10/2000 | Semlitsch |
| 6,146,421 A | 11/2000 | Gordon et al. |
| 6,162,252 A | 12/2000 | Kuras et al. |
| 6,179,874 B1 | 1/2001 | Cauthen |
| 6,206,929 B1 * | 3/2001 | Ochoa et al. ............... 623/22.17 |
| 6,217,249 B1 | 4/2001 | Merlo |
| 6,368,350 B1 | 4/2002 | Erickson et al. |
| 6,375,682 B1 | 4/2002 | Fleischmann et al. |
| 6,494,916 B1 | 12/2002 | Babalola et al. |
| 6,660,040 B2 | 12/2003 | Chan et al. |
| RE038,409 E | 1/2004 | Noiles |
| 6,740,117 B2 | 5/2004 | Ralph et al. |
| 6,740,118 B2 | 5/2004 | Eisermann et al. |
| 6,770,095 B2 | 8/2004 | Grinberg et al. |
| 6,893,465 B2 | 5/2005 | Huang |
| 6,942,701 B2 * | 9/2005 | Taylor ........................ 623/22.14 |
| 6,949,105 B2 | 9/2005 | Bryan et al. |
| 6,964,686 B2 | 11/2005 | Gordon |
| 6,981,989 B1 | 1/2006 | Fleischmann et al. |
| 6,981,991 B2 | 1/2006 | Ferree |
| 7,001,433 B2 | 2/2006 | Songer et al. |
| 7,060,099 B2 | 6/2006 | Carli et al. |
| 7,083,650 B2 | 8/2006 | Mockowitz et al. |
| 7,083,651 B2 | 8/2006 | Diaz et al. |
| 7,121,755 B2 | 10/2006 | Schlapfer et al. |
| 7,153,325 B2 | 12/2006 | Kim et al. |
| 7,179,294 B2 | 2/2007 | Eisermann et al. |
| 7,214,243 B2 | 5/2007 | Taylor |
| 7,214,244 B2 | 5/2007 | Zubok et al. |
| 7,250,060 B2 | 7/2007 | Trieu |
| 7,270,679 B2 | 9/2007 | Istephanous et al. |
| 7,276,082 B2 | 10/2007 | Zdeblick et al. |
| 7,326,250 B2 | 2/2008 | Beaurain et al. |
| 7,407,513 B2 | 8/2008 | Alleyne et al. |
| 7,442,211 B2 | 10/2008 | de Villiers et al. |
| 7,468,079 B2 | 12/2008 | Collier |
| 7,470,287 B2 | 12/2008 | Tornier et al. |
| 7,485,145 B2 | 2/2009 | Purcell |
| 7,494,507 B2 | 2/2009 | Dixon et al. |
| 7,531,002 B2 | 5/2009 | Sutton et al. |
| 7,537,615 B2 | 5/2009 | Lemaire |
| 7,550,009 B2 | 6/2009 | Arnin et al. |
| 7,550,010 B2 | 6/2009 | Humphreys et al. |
| 7,582,115 B2 | 9/2009 | Weber |
| 7,618,439 B2 | 11/2009 | Zubok et al. |
| 7,618,459 B2 | 11/2009 | Justin et al. |
| 7,621,956 B2 | 11/2009 | Paul et al. |
| 2002/0111682 A1 | 8/2002 | Ralph et al. |
| 2003/0055500 A1 | 3/2003 | Fell et al. |
| 2003/0114935 A1 | 6/2003 | Chan et al. |
| 2003/0191534 A1 | 10/2003 | Viart et al. |
| 2003/0220691 A1 | 11/2003 | Songer et al. |
| 2004/0010316 A1 | 1/2004 | William et al. |
| 2004/0034433 A1 | 2/2004 | Chan et al. |
| 2004/0073311 A1 | 4/2004 | Ferree |
| 2004/0088052 A1 | 5/2004 | Dearnaley |
| 2004/0117021 A1 | 6/2004 | Biedermann et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0172021 A1 | 9/2004 | Khalili |
| 2004/0220674 A1 | 11/2004 | Pria |
| 2004/0267374 A1 | 12/2004 | Friedrichs |
| 2004/0267375 A1 | 12/2004 | Friedrichs |
| 2005/0004572 A1 | 1/2005 | Biedermann et al. |
| 2005/0015152 A1 | 1/2005 | Sweeney |
| 2005/0021145 A1 | 1/2005 | de Villiers et al. |
| 2005/0038516 A1 | 2/2005 | Spoonamore |
| 2005/0071007 A1 | 3/2005 | Malek |
| 2005/0080488 A1 | 4/2005 | Schultz |
| 2005/0113926 A1 | 5/2005 | Zucherman et al. |
| 2005/0113931 A1 * | 5/2005 | Horber ....................... 623/19.14 |
| 2005/0125065 A1 | 6/2005 | Zucherman et al. |
| 2005/0165485 A1 | 7/2005 | Trieu |
| 2005/0197706 A1 | 9/2005 | Hovorka et al. |
| 2005/0203626 A1 | 9/2005 | Sears et al. |
| 2005/0216081 A1 | 9/2005 | Taylor |
| 2005/0251261 A1 | 11/2005 | Peterman |
| 2005/0251262 A1 | 11/2005 | De Villiers et al. |
| 2006/0020342 A1 | 1/2006 | Ferree et al. |
| 2006/0025862 A1 | 2/2006 | Villiers et al. |
| 2006/0041314 A1 | 2/2006 | Millard |
| 2006/0085076 A1 | 4/2006 | Krishna et al. |
| 2006/0129240 A1 | 6/2006 | Lessar et al. |
| 2006/0136062 A1 | 6/2006 | DiNello et al. |
| 2006/0178744 A1 | 8/2006 | de Villiers et al. |
| 2006/0190079 A1 | 8/2006 | Istephanous et al. |
| 2006/0200247 A1 | 9/2006 | Charrois |
| 2006/0217809 A1 | 9/2006 | Albert et al. |
| 2006/0235527 A1 | 10/2006 | Buettner-Janz et al. |
| 2006/0241766 A1 | 10/2006 | Felton et al. |
| 2006/0259147 A1 | 11/2006 | Krishna et al. |
| 2006/0271200 A1 | 11/2006 | Greenlee |
| 2006/0293752 A1 | 12/2006 | Moumene et al. |
| 2007/0021837 A1 | 1/2007 | Ashman |
| 2007/0032875 A1 | 2/2007 | Blacklock et al. |
| 2007/0032877 A1 | 2/2007 | Whiteside |
| 2007/0050032 A1 | 3/2007 | Gittings et al. |
| 2007/0073405 A1 | 3/2007 | Verhulst et al. |
| 2007/0083267 A1 | 4/2007 | Miz et al. |
| 2007/0100454 A1 | 5/2007 | Burgess et al. |
| 2007/0100456 A1 | 5/2007 | Dooris et al. |
| 2007/0106391 A1 | 5/2007 | Ronk |
| 2007/0118223 A1 | 5/2007 | Allared et al. |
| 2007/0168037 A1 | 7/2007 | Posnick |
| 2007/0173936 A1 | 7/2007 | Hester et al. |
| 2007/0185578 A1 | 8/2007 | O'Neil et al. |
| 2007/0213821 A1 | 9/2007 | Kwak et al. |
| 2007/0233244 A1 | 10/2007 | Lopez et al. |
| 2007/0239276 A1 | 10/2007 | Squires et al. |
| 2008/0065211 A1 | 3/2008 | Albert et al. |
| 2008/0065216 A1 | 3/2008 | Hurlbert et al. |
| 2008/0071381 A1 | 3/2008 | Buscher et al. |
| 2008/0077137 A1 | 3/2008 | Balderston |
| 2008/0133017 A1 | 6/2008 | Beyar et al. |
| 2008/0154263 A1 | 6/2008 | Janowski et al. |
| 2008/0154369 A1 | 6/2008 | Barr et al. |
| 2008/0161930 A1 | 7/2008 | Carls et al. |
| 2008/0195212 A1 | 8/2008 | Nguyen et al. |
| 2008/0215156 A1 | 9/2008 | Duggal et al. |
| 2008/0221689 A1 | 9/2008 | Chaput et al. |
| 2008/0221690 A1 | 9/2008 | Chaput et al. |
| 2008/0228276 A1 | 9/2008 | Mathews et al. |
| 2008/0243253 A1 | 10/2008 | Levieux |
| 2008/0300685 A1 | 12/2008 | Carls et al. |
| 2009/0005872 A1 | 1/2009 | Moumene et al. |
| 2009/0012619 A1 | 1/2009 | Cordaro et al. |
| 2009/0043391 A1 | 2/2009 | de Villiers et al. |
| 2009/0054986 A1 | 2/2009 | Cordaro et al. |
| 2009/0062920 A1 | 3/2009 | Tauber |

| | | | |
|---|---|---|---|
| 2009/0076614 A1 | 3/2009 | Arramon | |
| 2009/0082867 A1 | 3/2009 | Sebastian Bueno et al. | |
| 2009/0105758 A1 | 4/2009 | Gimbel et al. | |
| 2009/0138090 A1 | 5/2009 | Hurlbert et al. | |
| 2009/0192616 A1 | 7/2009 | Zielinski | |
| 2009/0192617 A1 | 7/2009 | Arramon et al. | |
| 2009/0215111 A1 | 8/2009 | Veenstra et al. | |
| 2009/0234458 A1 | 9/2009 | de Villiers et al. | |
| 2009/0248161 A1 | 10/2009 | Theofilos et al. | |
| 2009/0270986 A1 | 10/2009 | Christensen | |
| 2009/0276051 A1 | 11/2009 | Arramon et al. | |
| 2009/0281629 A1* | 11/2009 | Roebling et al. | 623/17.16 |
| 2010/0030335 A1 | 2/2010 | Arramon | |
| 2010/0063589 A1* | 3/2010 | Tepic | 623/17.11 |
| 2010/0063597 A1 | 3/2010 | Gradel | |
| 2010/0161072 A1 | 6/2010 | Drescher | |

FOREIGN PATENT DOCUMENTS

| | | |
|---|---|---|
| WO | 9738650 | 11/1997 |
| WO | 0023015 | 4/2000 |
| WO | 2005039455 | 5/2005 |
| WO | 2006069465 | 7/2006 |
| WO | 2007087730 | 8/2007 |
| WO | 2008088777 | 7/2008 |
| WO | 2008094260 | 8/2008 |
| WO | 2009105884 | 9/2009 |
| WO | 2009126908 | 10/2009 |

OTHER PUBLICATIONS

Clewlow, J.P., Pylios, T. and Shepherd, D.E.T., "Soft Layer Bearing Joins for Spine Arthroplasty", vol. 29, No. 10, Dec. 2008, pp. 1981-1985, "Materials and Design", Edgabaston, UK.

Parea, Philippe E., Chana, Frank W., Bhattacharyab, Sanghita and Goelb, Vijay K., "Surface Slide Track Mapping of Implants for Total Disc Arthroplasty", vol. 42, No. 2, Jan. 19, 2009, pp. 131-139, "Journal of Biomechanics", [online] [retrieved Feb. 19, 2010].

Dooris, Andrew P., Goel, Vijay K., Todd, Dwight T., Grosland, Nicole M., Wilder, David G., "Load Sharing in a Lumbar Motion Segment Implanted with an Artificial Disc Under Combined Sagittal Plane Loading", BED-vol. 42, 1999, pp. 277-278, American Society of Mechanical Engineers, Iowa City, Iowa.

* cited by examiner

PROSTHETIC JOINT

CROSS-REFERENCE TO RELATED APPLICATIONS

This application is a Continuation-in-Part of application Ser. No. 11/936,601, filed Nov. 7, 2007, which is currently pending.

BACKGROUND OF THE INVENTION

This invention relates generally to medical implants, and more particularly to prosthetic joints having conformal geometries and wear resistant properties.

Medical implants, such as knee, hip, and spine orthopedic replacement joints and other joints and implants have previously consisted primarily of a hard metal motion element that engages a polymer contact pad. This has usually been a high density high wear resistant polymer, for example Ultra-High Molecular Weight Polyethylene (UHMWPE), or other resilient material. The problem with this type of configuration is the polymer eventually begins to degrade due to the caustic nature of blood, the high impact load, and high number of load cycles. As the resilient member degrades, pieces of polymer may be liberated into the joint area, often causing accelerated wear, implant damage, and tissue inflammation and harm.

It is desirable to employ a design using a hard member on a hard member (e.g. metals or ceramics), thus eliminating the polymer. Such a design is expected to have a longer service life. Extended implant life is important as it is now often required to revise or replace implants. Implant replacement is undesirable from a cost, inconvenience, patient health, and resource consumption standpoint.

Implants using two hard elements of conventional design will be, however, subject to rapid wear. First, a joint having one hard, rigid element on another will not be perfectly shaped to a nominal geometry. Such imperfections will result in points of high stress, thus causing localized wear. Furthermore, two hard elements would lack the resilient nature of a natural joint. Natural cartilage has a definite resilient property, absorbing shock and distributing periodic elevated loads. This in turn extends the life of a natural joint and reduces stress on neighboring support bone and tissue. If two rigid members are used, this ability to absorb the shock of an active lifestyle could be diminished. The rigid members would transmit the excessive shock to the implant to bone interface. Some cyclical load in these areas stimulates bone growth and strength; however, excessive loads or shock stress or impulse loading the bone-to-implant interface will result in localized bone mass loss, inflammation, and reduced support.

BRIEF SUMMARY OF THE INVENTION

These and other shortcomings of the prior art are addressed by the present invention, which provides a prosthetic joint having wear-resistant contacting surfaces with conformal properties.

According to one aspect of the invention, a prosthetic joint includes: (a) a first bone-implantable member comprising a rigid material and including a body having an annular flange extending outward at a first end thereof, the first end of the body and the flange cooperatively defining a wear-resistant, concave first contact surface having a protruding rim and a recessed central portion; and (b) a second bone-implantable member comprising a rigid material with a wear-resistant, convex second contact surface; (c) where the first and second contact surfaces bear directly against each other so as to transfer axial and lateral loads from one of the members to the other, while allowing pivoting motion between the two members; and (d) wherein the flange is shaped so as to deform elastically and permit the first contact surface to conform to the second contact surface when the joint is placed under a predetermined load.

BRIEF DESCRIPTION OF THE DRAWINGS

The invention may be best understood by reference to the following description taken in conjunction with the accompanying drawing figures in which.

DETAILED DESCRIPTION OF THE INVENTION

The present invention provides a specialized implant contact interface (implant geometry). In this geometry, an implanted joint includes two typically hard (i.e. metal or ceramic) members; however, at least one of the members is formed such that it has the characteristics of a resilient member, such as: the ability to absorb an impact load; the ability to absorb high cycle loading (high endurance limit); the ability to be self cleaning; and the ability to function as a hydrodynamic and/or hydrostatic bearing.

Generally, the contact resilient member is flexible enough to allow elastic deformation and avoid localized load increases, but not so flexible as to risk plastic deformation, cracking and failure. In particular, the resilient member is designed such that the stress levels therein will be below the high-cycle fatigue endurance limit. As an example, the resilient member might be only about 10% to about 20% as stiff as a comparable solid member. It is also possible to construct the resilient member geometry with a variable stiffness, i.e. having a low effective spring rate for small deflections and a higher rate as the deflections increase, to avoid failure under sudden heavy loads.

Figure 1:
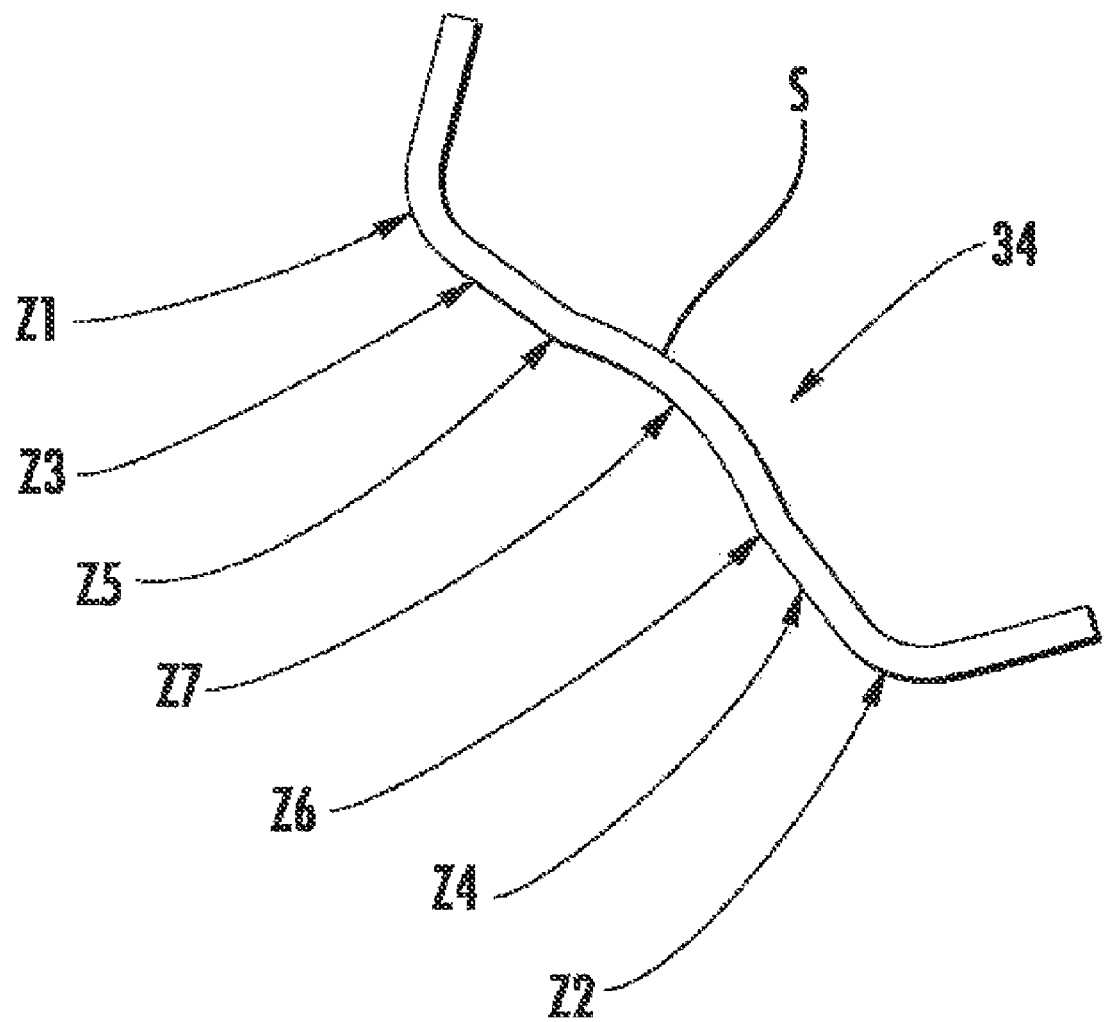
FIG. 1 is a cross-sectional view of a portion of a resilient contact member constructed in accordance with the present invention.

FIG. 1 illustrates an exemplary contact member 34 including a basic resilient interface geometry. The contact member 34 is representative of a portion of a medical implant and is made of one or more metals or ceramics (for example, partially stabilized Zirconia). It may be coated as described below. The geometry includes a lead-in shape, Z1 and Z2, a contact shape, Z3 and Z4, a lead-out shape, Z5 and Z6, and a relieved shape, Z7. It may be desired to vary the cross-sectional thickness to achieve a desired mechanical stiffness to substrate resilience characteristic. The presence of the relieved region Z7 introduces flexibility into the contact member 34, reduces the potential for concentrated point contact with a mating curved member, and provides a reservoir for a working fluid.

The Z7 region may be local to the contact member 34 or may be one of several. In any case, it may contain a means of providing fluid pressure to the internal contact cavity to produce a hydrostatic interface. A passive (powered by the regular motion of the patient) or active (powered by micro components and a dedicated subsystem) pumping means and optional filtration may be employed to provide the desired fluid interaction.

A hydrodynamic interface is desirable as, by definition, it means the contact member 34 is not actually touching the mating joint member. The lead-in and lead-out shapes Z1, Z2, Z5, Z6 are configured to generate a shear stress in the working fluid so as to create the fluid "wedge" of a hydrodynamic support.

Figure 2:
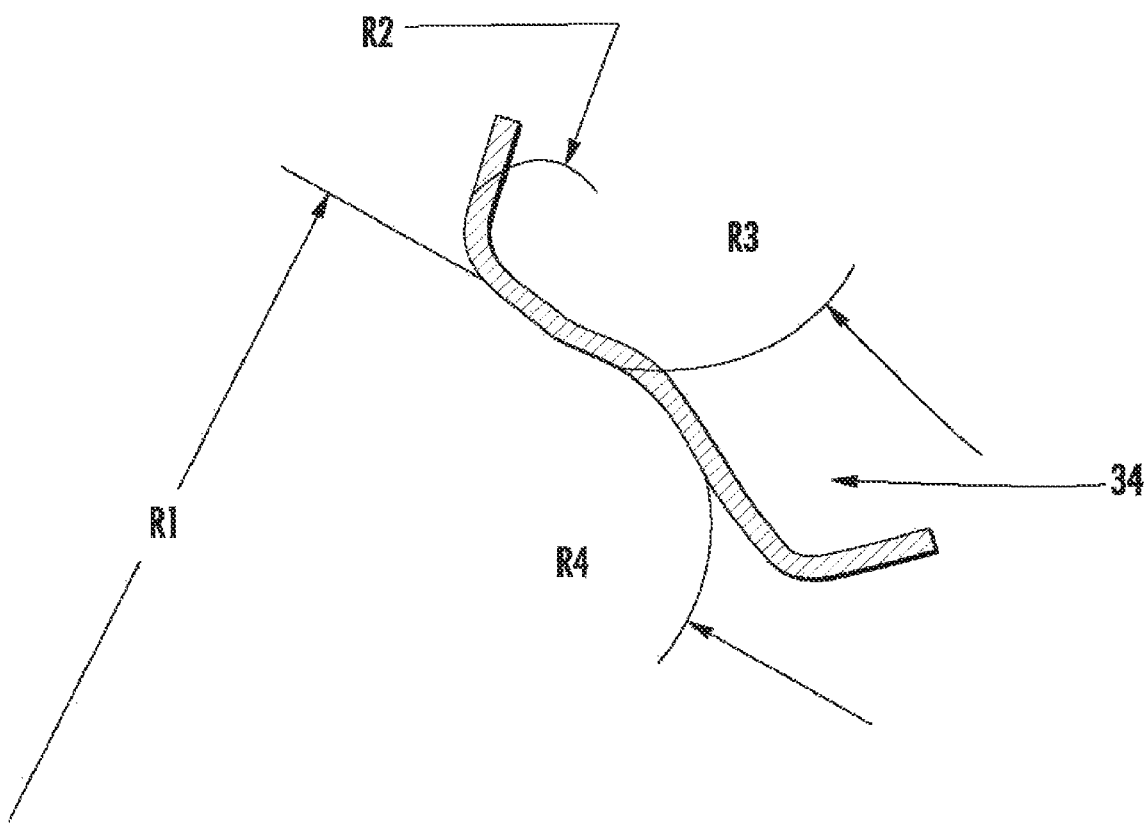
FIG. 2 is an enlarged view of the contact member of FIG. 1 in contact with a mating joint member.
Figure 3:
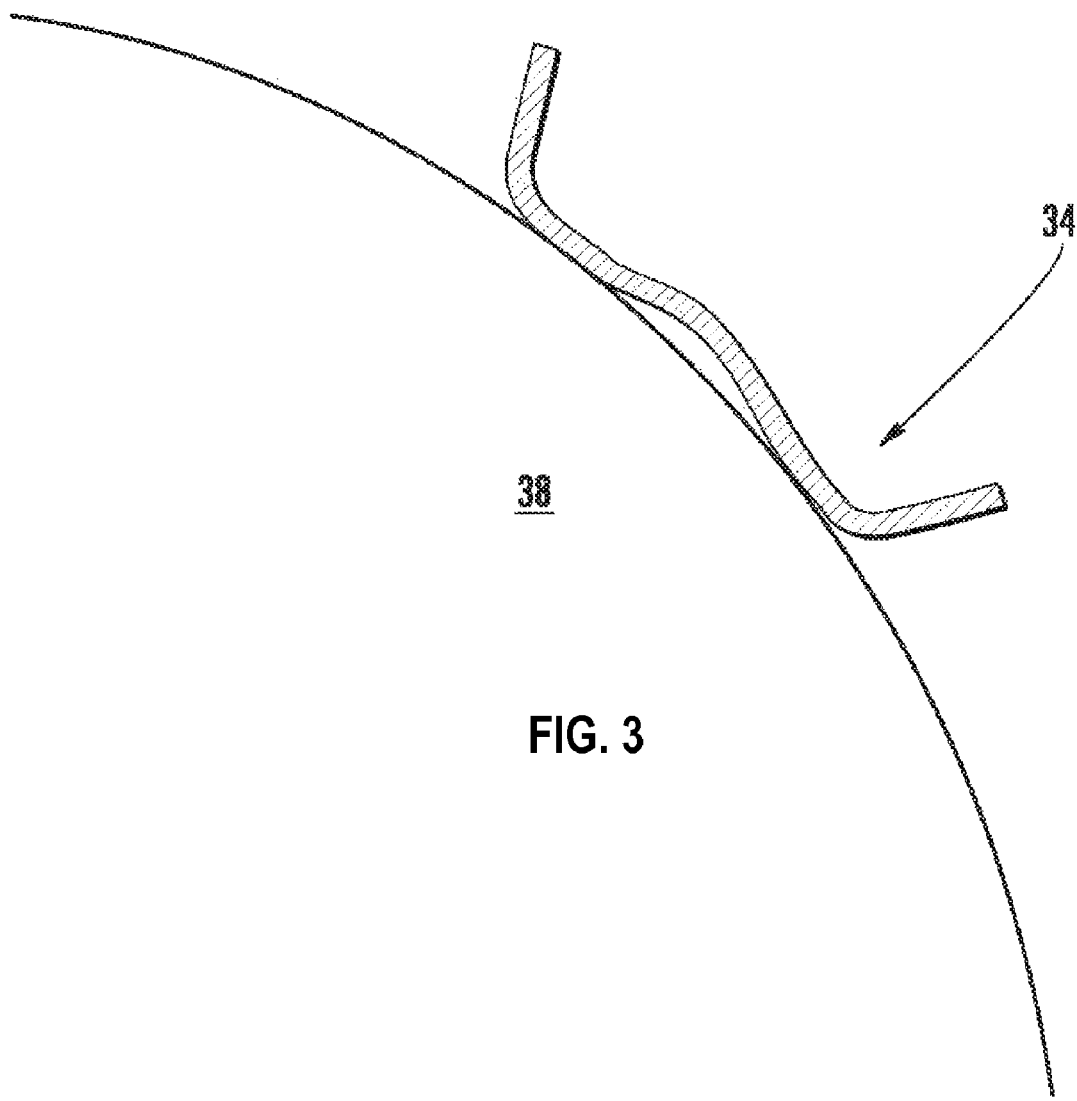
FIG. 3 is a side view of a resilient contact member in contact with a mating joint member.

FIG. 2 shows a closer view of the contact member 34. It may be desirable to make the contact radius (Z3 and Z4) larger or smaller, depending on the application requirement and flexural requirement. For example, FIG. 3 illustrates the contact member 34 in contact with a mating joint member 38 having a substantially larger radius than the contact member 34. The radius ratio between the two joint members is not particularly critical, so long as one of the members exhibits the resilient properties described herein.

The contact member 34 includes an osseointegration surface "S", which is a surface designed to be infiltrated by bone growth to improve the connection between the implant and the bone. Osseointegration surfaces may be made from materials such as TRABECULAR METAL, textured metal, or sintered or extruded implant integration textures. TRABECULAR METAL is an open metal structure with a high porosity (e.g. about 80%) and is available from Zimmer, Inc., Warsaw, Ind. 46580 USA.

Figure 4:
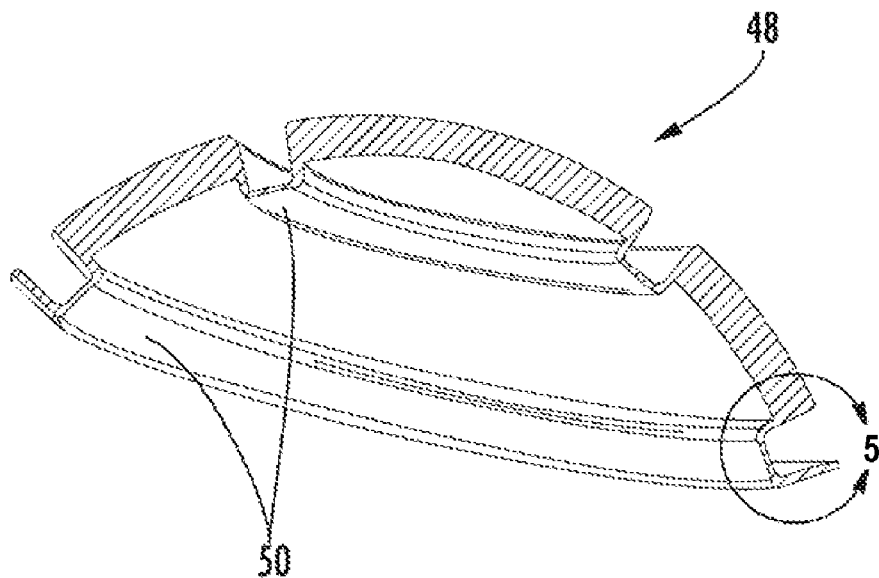
FIG. 4 is a cross-sectional view of a cup for an implant according to an alternate embodiment of the invention.
Figure 5:
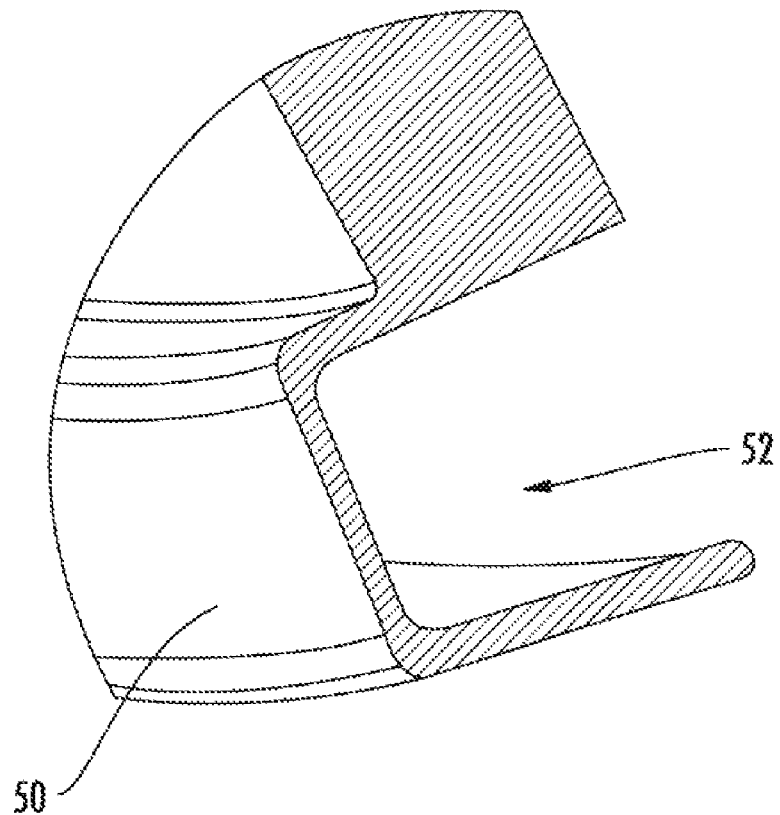
FIG. 5 is an enlarged view of a portion of the cup of FIG. 4.
Figure 6:
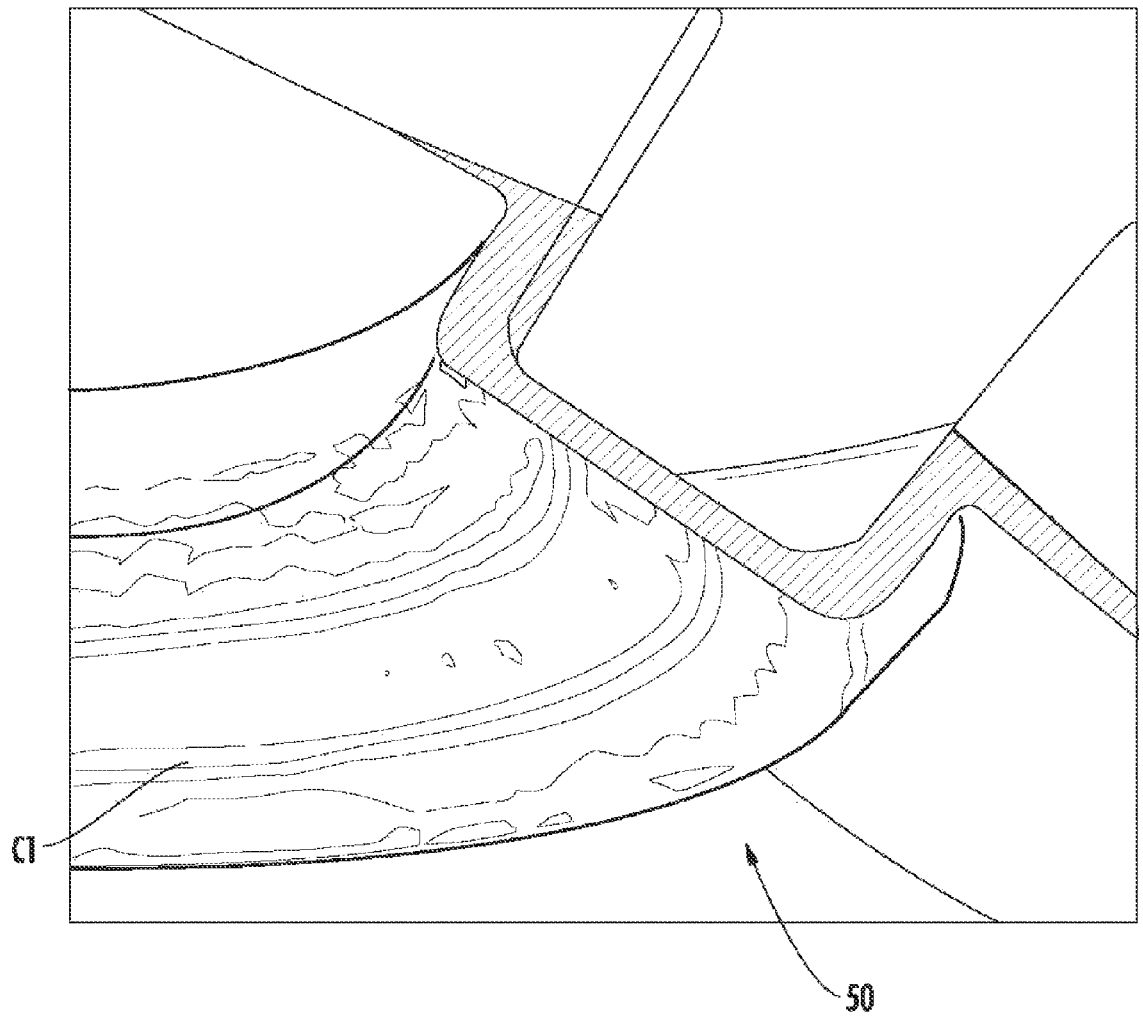
FIG. 6 is a perspective view of a finite element model of a joint member.

FIGS. 4 and 5 illustrate a cup 48 of metal or ceramic with two integrally-formed contact rings 50. More contact rings may be added if needed. As shown in FIG. 5, the volume behind the contact rings 50 may be relieved. This relieved area 52 may be shaped so as to produce a desired balance between resilience and stiffness. A varying cross-section geometry defined by varying inner and outer spline shapes may be desired. In other words, a constant thickness is not required. A material such as a gel or non-Newtonian fluid (not shown) may be disposed in the relieved area 52 to modify the stiffness and damping characteristics of the contact rings 50 as needed for a particular application. The cup 48 could be used as a stand-alone portion of a joint, or it could be positioned as a liner within a conventional liner. The contact ring 50 is shown under load in FIG. 6, which depicts contour lines of highest compressive stress at "C1". This is the portion of the contact ring 50 that would be expected to undergo bending first. The bearing interface portion of the resilient contact member could be constructed as a bridge cross-section supported on both sides as shown or as a cantilevered cross-section depending on the desired static and dynamic characteristics.

Figure 8:
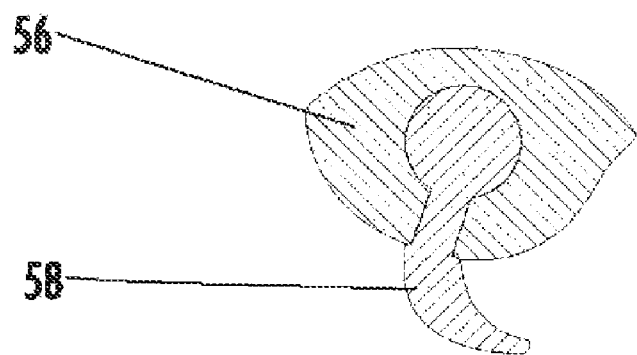
FIG. 8 is an enlarged view of a portion of FIG. 7.
Figure 7:
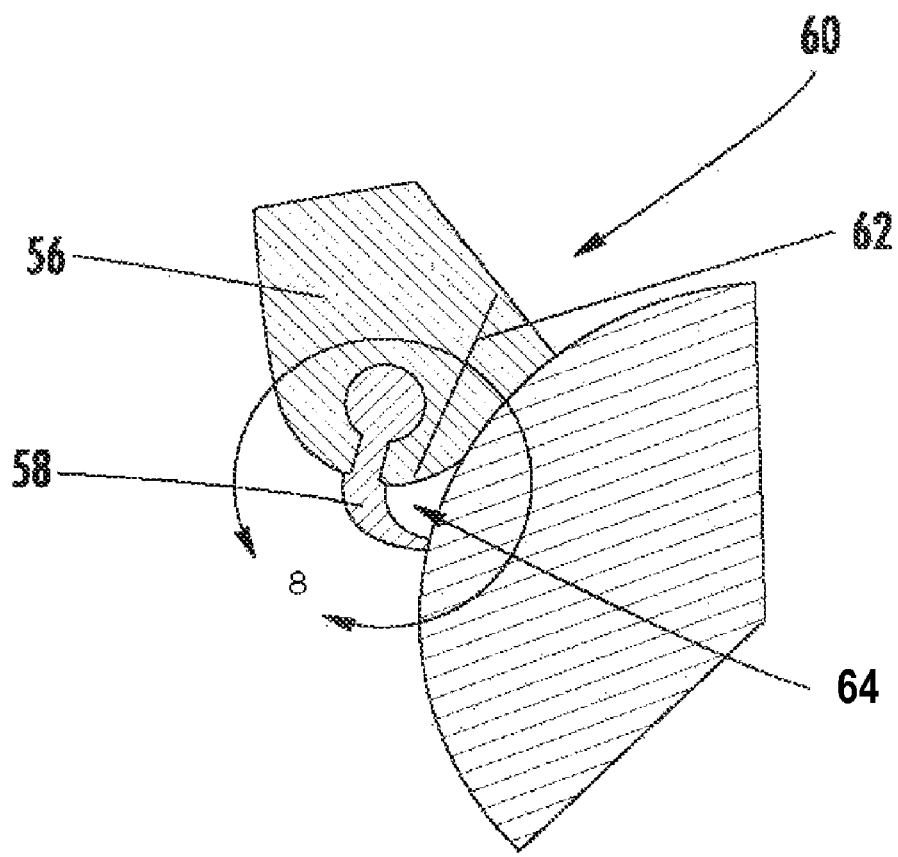
FIG. 7 is a cross-sectional view of an implant joint including a flexible seal.
Figure 9:
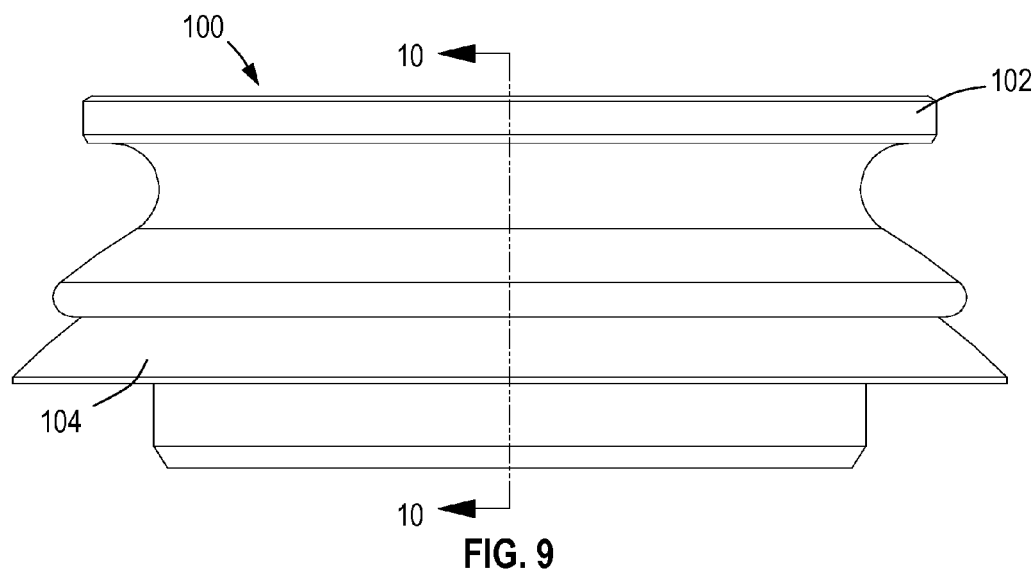
FIG. 9 is a side view of a prosthetic joint constructed in accordance with an aspect of the present invention.

FIGS. 7 and 8 illustrate an implant 56 of rigid material which includes a wiper seal 58. The wiper seal 58 keeps particles out of the contact area (seal void) 60 of the implant 58, and working fluid (natural or synthetic) in. The seal geometry is intended to be representative and a variety of seal characteristics may be employed; such as a single lip seal, a double or multiple lip seal, a pad or wiper seal made from a variety of material options. Different seal mounting options may be used, for example a lobe in a shaped groove as shown in FIGS. 7 and 8, a retaining ring or clamp, or an adhesive. The wiper seal 58 may also be integrated into the contact face of the interface zone.

It may be desirable to create a return passage 62 from the seal void region 60 back into the internal zone 64 in order to stabilize the pressure between the two and to allow for retention of the internal zone fluid if desired. This is especially relevant when the hydrostatic configuration is considered.

Figure 10:
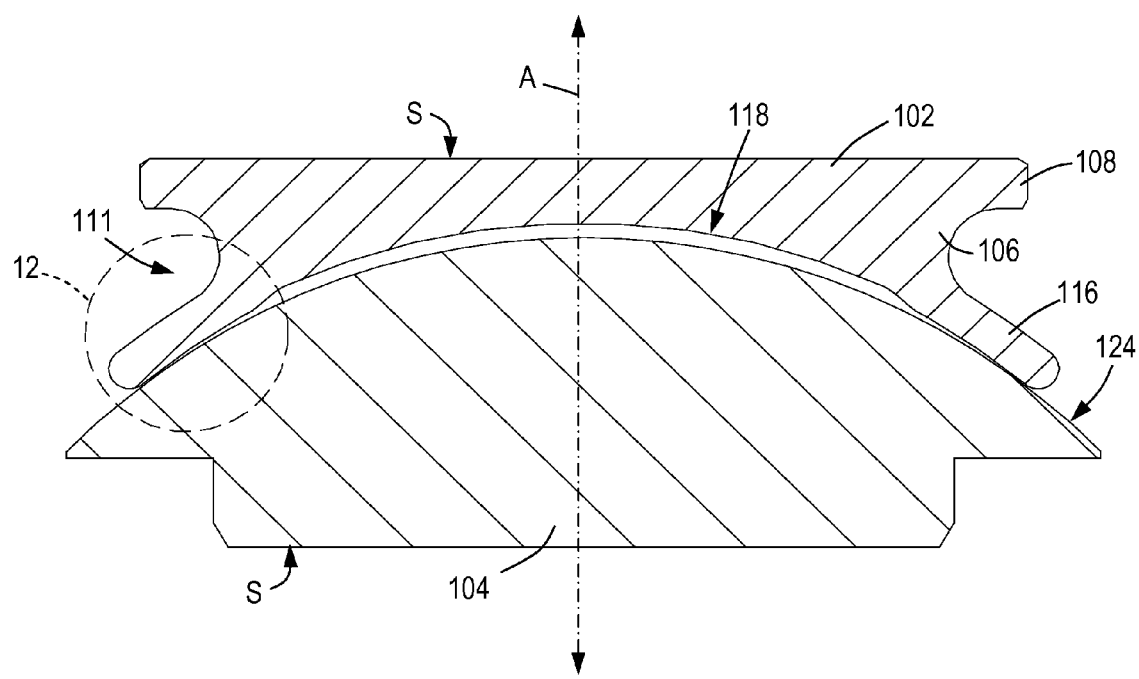
FIG. 10 is a cross-sectional view of the prosthetic joint of FIG. 9 in an unloaded condition.
Figure 11:
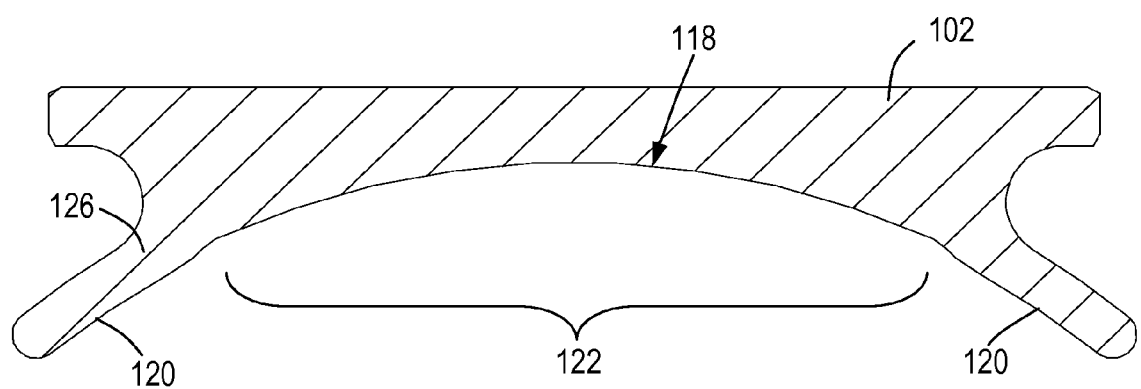
FIG. 11 is a cross-sectional view of one of the members of the prosthetic joint of FIG. 9.

FIGS. 9-14 illustrate a prosthetic joint 100 comprising first and second members 102 and 104. The illustrated prosthetic joint 100 is particularly adapted for a spinal application, but it will be understood that the principles described herein may be applied to any type of prosthetic joint. Both of the members 102 and 104 are bone-implantable, meaning they include osseointegration surfaces, labeled "S", which are surfaces designed to be infiltrated by bone growth to improve the connection between the implant and the bone. Osseointegration surfaces may be made from materials such as TRABECULAR METAL, textured metal, or sintered or extruded implant integration textures, as described above. As shown in FIG. 10, a central axis "A" passes through the centers of the first and second members 102 and 104 and is generally representative of the direction in which external loads are applied to the joint 100 in use. In the illustrated examples, the first and second joint members are bodies of revolution about this axis, but the principles of the present invention also extend to shapes that are not bodies of revolution.

The first member 102 includes a body 106 with a perimeter flange 116 extending in a generally radially outward direction at one end. Optionally, a disk-like base 108 may be disposed at the end of the body 106 opposite the flange 116, in which case a circumferential gap 111 will be defined between the base 106 and the flange 116. The first member 102 is constructed from a rigid material. As used here, the term "rigid" refers to a material which has a high stiffness or modulus of elasticity. Nonlimiting examples of rigid materials having appropriate stiffness for the purpose of the present invention include stainless steels, cobalt-chrome alloys, titanium, aluminum, and ceramics. By way of further example, materials such as polymers would generally not be considered "rigid" for the purposes of the present invention. Generally, a rigid material should have a modulus of elasticity of about $0.5 \times 10^6$ psi or greater. Collectively, one end of the body 106 and the flange 116 define a wear-resistant, concave first contact surface 118. As used herein, the term "wear-resistant" refers to a material which is resistant to surface material loss when placed under load. Generally the wear rate should be no more than about 0.5 μm (0.000020 in.) to about 1.0 μm (0.000040 in.) per million cycles when tested in accordance with ASTM Guide F2423. As a point of reference, it is noted that any of the natural joints in a human body can easily experience one million operating cycles per year. Nonlimiting examples of wear-resistant materials include solid metals and ceramics. Known coatings such as titanium nitride, chrome plating, carbon thin films, and/or diamond-like carbon coatings may be used to impart wear resistance to the first contact surface 118. Optionally, the first contact surface 118 could comprise a separate face layer (not shown) of a wear-resistant material such as ultra-high molecular weight (UHMW) polyurethane.

Figure 14:
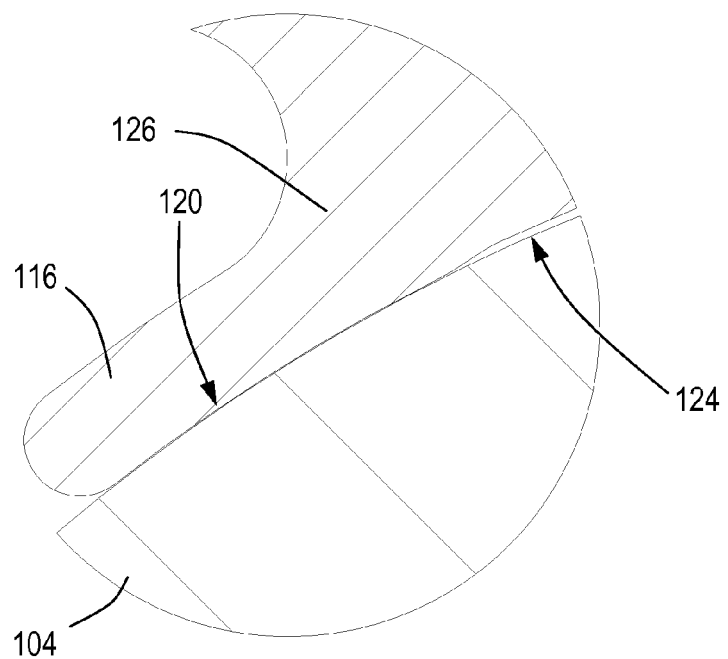
FIG. 14 is an enlarged view of a portion of FIG. 13.
Figure 15:
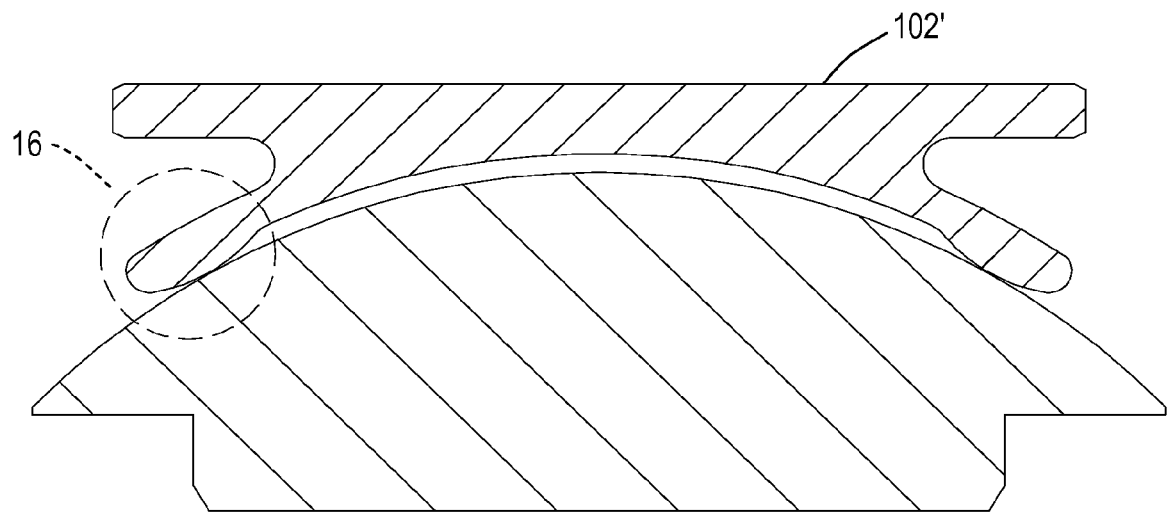
FIG. 15 is a cross-sectional view of an alternative joint member.
Figure 16:
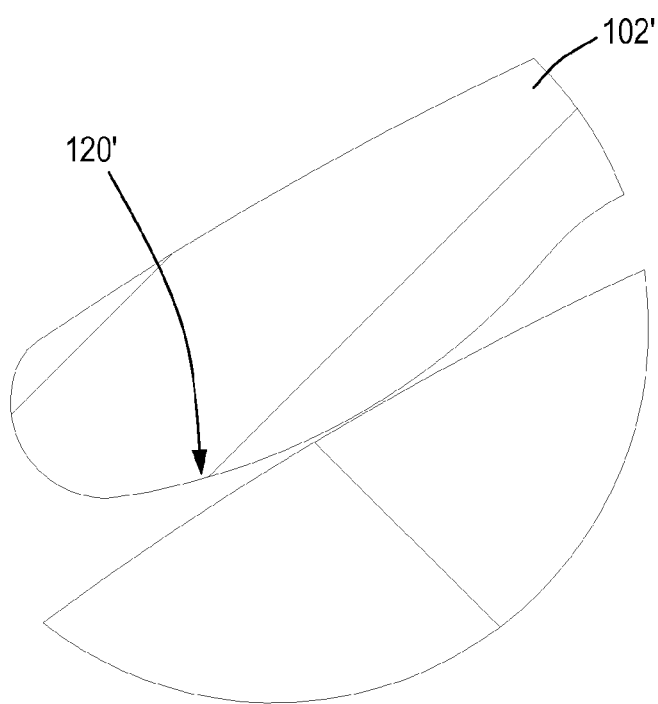
FIG. 16 is an enlarged view of a portion of FIG. 15.

The first contact surface 118 includes a protruding peripheral rim 120 (see FIG. 11), and a recessed central portion 122, which may also be considered a "pocket" or a "relief". As used herein, the term "recessed" as applied to the central portion 122 means that the central portion 122 lies outside of the nominal exterior surface of the second member 104 when the joint 100 is assembled. In one configuration, shown in FIGS. 9-14, and best seen in FIG. 11, the rim 120 is concave, with the radius of curvature being quite high, such that the cross-sectional shape of the surface of the rim 120 approaches a straight line. FIGS. 15 and 16 show another configuration of a joint member 102' in which the rim 120' has a convex-curved cross-sectional shape. The cross-sectional shape of the rim may be flat or curved as necessary to suit a particular application.

The annular configuration of first contact surface 118 with the protruding rim 120 results in a configuration which permits only pivoting and rotational motion, and is statically and dynamically determinate for the life of the joint 100. In contrast, prior art designs employing mating spherical shapes, even very accurate shapes, quickly reach a statically and dynamically indeterminate condition after use and wear. This condition accelerates wear, contributes to the fretting corrosion wear mechanism, and permits undesired lateral translation between the joint members.

The second member 104 is also made from a rigid material and has a wear-resistant, convex second contact surface 124. The first and second contact surfaces 118 and 124 bear directly against each other so as to transfer axial and lateral loads from one member to the other while allowing pivoting motion between the two members 102 and 104.

Nominally the first and second members 102 and 104 define a "ring" or "band" contact interface therebetween. In practice it is impossible to achieve surface profiles completely free of minor imperfections and variations. If the first and second members 102 and 104 were both completely rigid, this would cause high Hertzian contact stresses and rapid wear. Accordingly, an important feature of the illustrated joint 100 is that the flange 116 (and thus the first contact surface 118) of the first member 102 is conformable to the second contact surface 124 when the joint is placed under load.

Figure 12:
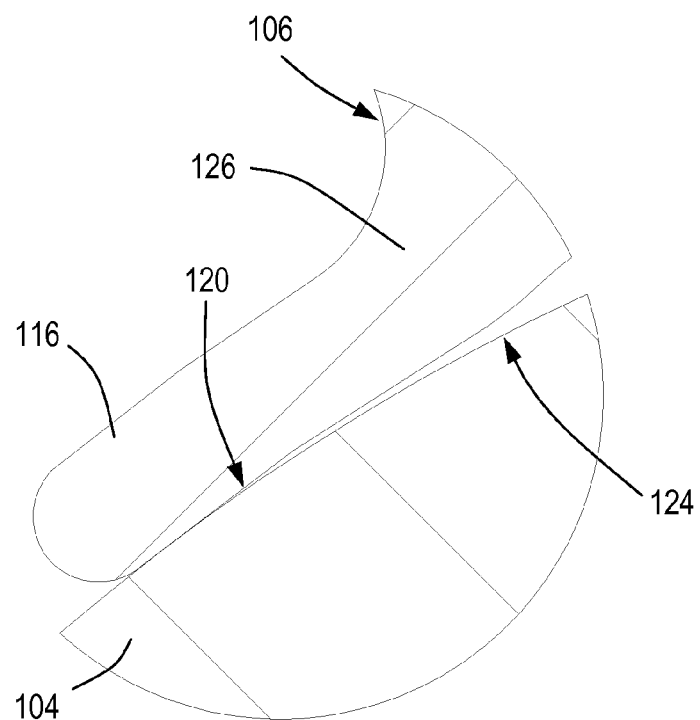
FIG. 12 is an enlarged view of a portion of FIG. 10.
Figure 13:
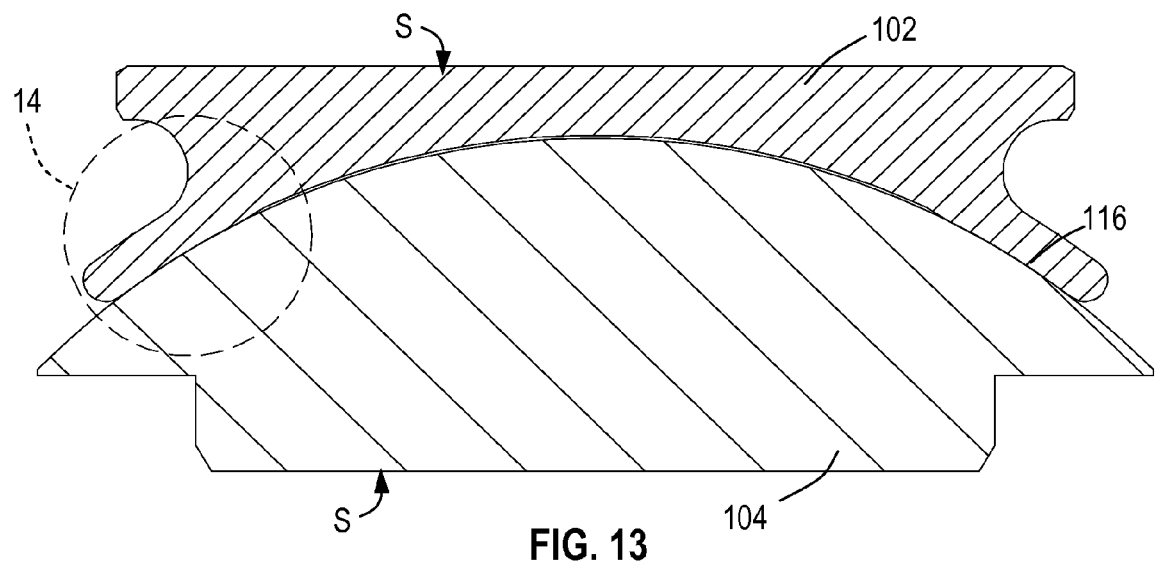
FIG. 13 is a cross-sectional view of the prosthetic joint of FIG. 9 in a loaded condition.

FIGS. 10 and 12 show a cross-sectional view of the flange 116 in an unloaded condition or free shape. It can be seen that the distal end of the rim 120 contacts the second contact surface 124, while the inboard end of the rim 120 (i.e. near where the flange 116 joins the body 106) does not. FIGS. 13 and 14 show the flange 116 in a deflected position or loaded shape, where substantially the entire section width of the rim 120 contacts the second contact surface 124, resulting in a substantially increased contact surface area between the two members 102 and 104, relative to the free shape. The rim 120' of the joint member 102' (see FIG. 16) is similarly conformable; however, given the curved cross-sectional shape, the total amount of surface contact area remains substantially constant in both loaded and unloaded conditions, with the rim 120' undergoing a "rolling" or "rocking" motion as the loading changes.

The conformable nature of the flange 116 is explained in more detail with reference to FIGS. 24 through 30. As noted above, the first member 102 has a flange 116 and a concave first contact surface 118. The second member 104 has a convex second contact surface 124. When assembled and in use the joint 100 is subject, among other loads, to axial loading in the direction of the arrows labeled "F" in FIG. 24 (i.e. along axis "A" of FIG. 10). As previously stated, it is impossible in practice for either of the contact surfaces 118 or 124 to be perfect surfaces (i.e. a perfect sphere or other curve or collection of curves). It is believed that in most cases that a defect such as a protrusion from the nominal contact surface of just 0.00127 mm (0.00005 in.), that is, 50 millionths of a inch, or larger, would be sufficient to cause fretting corrosion and failure of a metal-on-metal joint constructed to prior art standards. A defect may include a variance from a nominal surface shape as well as a discontinuity in the contact surface. Defects may arise through a variety of sources such as manufacturing, installation, and/or operating loads in the implanted joint.

Figure 25:
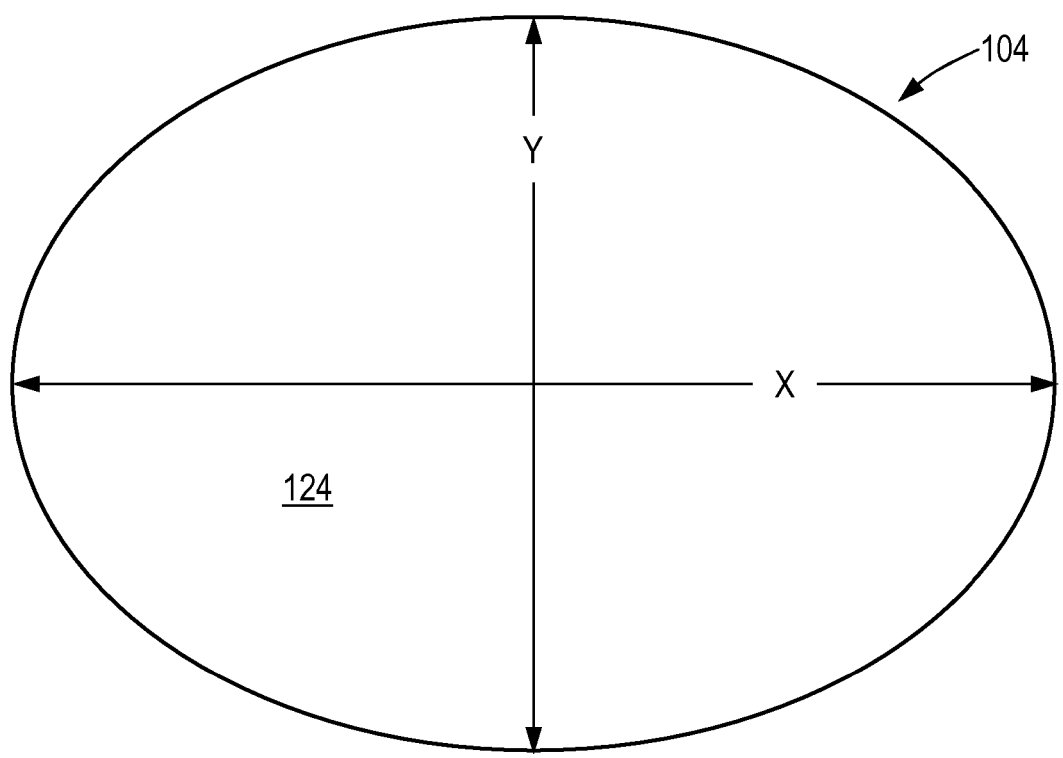
FIG. 25 is a top plan view of one of the joint members shown in FIG. 24.
Figure 26:
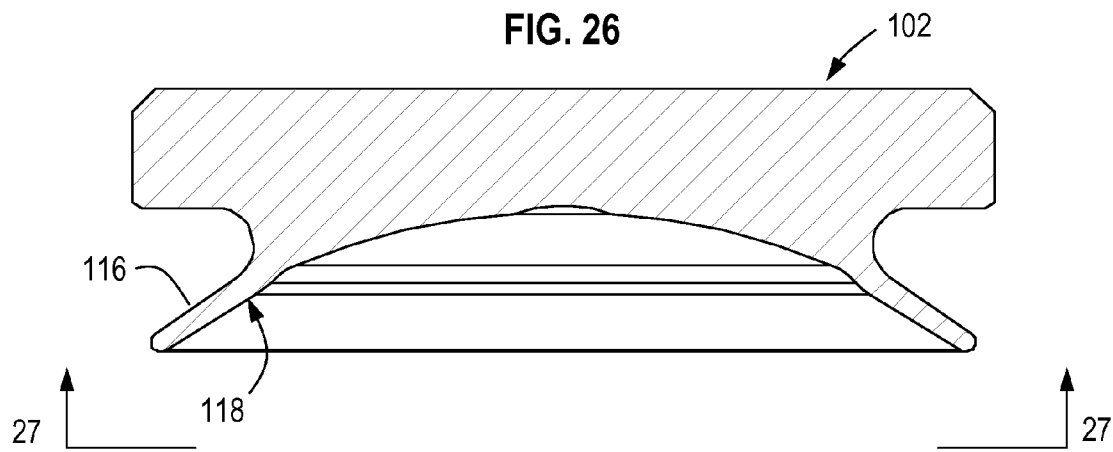
FIG. 26 is a cross-sectional view of one of the joint members shown in FIG. 24.
Figure 27:
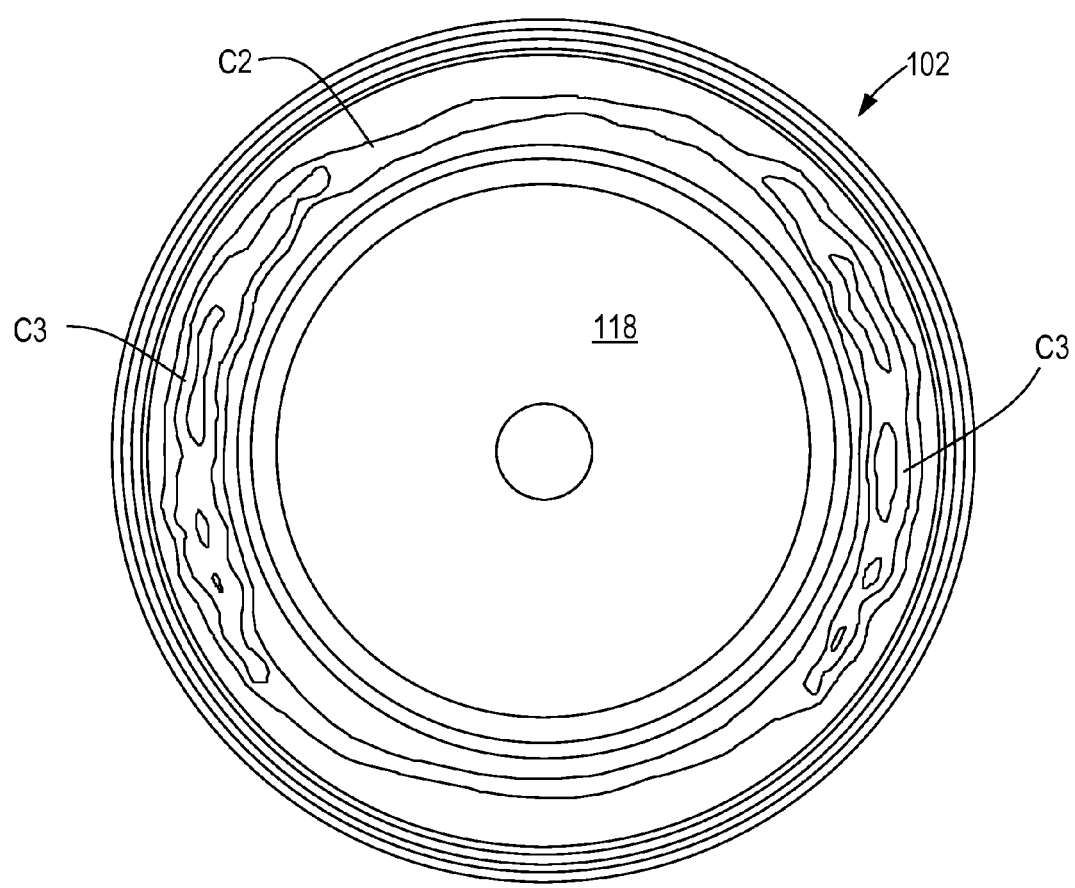
FIG. 27 is a contact stress plot of the joint member shown in FIG. 26.

FIG. 25 shows the second member 104 which in this particular example varies from a nominal shape in that it is elliptical rather than circular in plan view. The elliptical shape is grossly exaggerated for illustrative purposes. For reference, the dimensions of the second member 104 along the major axis labeled "X" is about 0.0064 mm (0.00025 in.) larger than its dimension along the minor axis labeled "Y". When assembled and loaded, the flange 116 conforms to the imperfect second contact surface 124 and deflects in an irregular shape. In other words, in addition to any uniform deflection which may be present, the deflected shape of the flange 116 includes one or more specific locations or portions that are deflected towards or away from the nominal free shape to a greater or lesser degree than the remainder of the flange 116. Most typically the deflected shape would be expected to be non-axisymmetric. For example, the deflection of the flange 116 at points located at approximately the three o'clock and nine o'clock positions is substantially greater than the deflection of the remainder of the flange 116. As a result, the contact stress in that portion of the first contact surface 118 is relieved. FIG. 27 is a plan view plot (the orientation of which is shown by arrow in FIG. 26) which graphically illustrates the expected contact stresses in the first contact surface 118 as determined by analytical methods. The first contour line "C2" shows that a very low level of contract stress is present around the entire perimeter of the first contact surface 118. This is because the entire first contact surface 118 is in contact with the second contact surface 124. Another contour line "C3" represents the areas of maximum contact stress corresponding to the protruding portions of the elliptical second contact surface 124.

Figure 28:
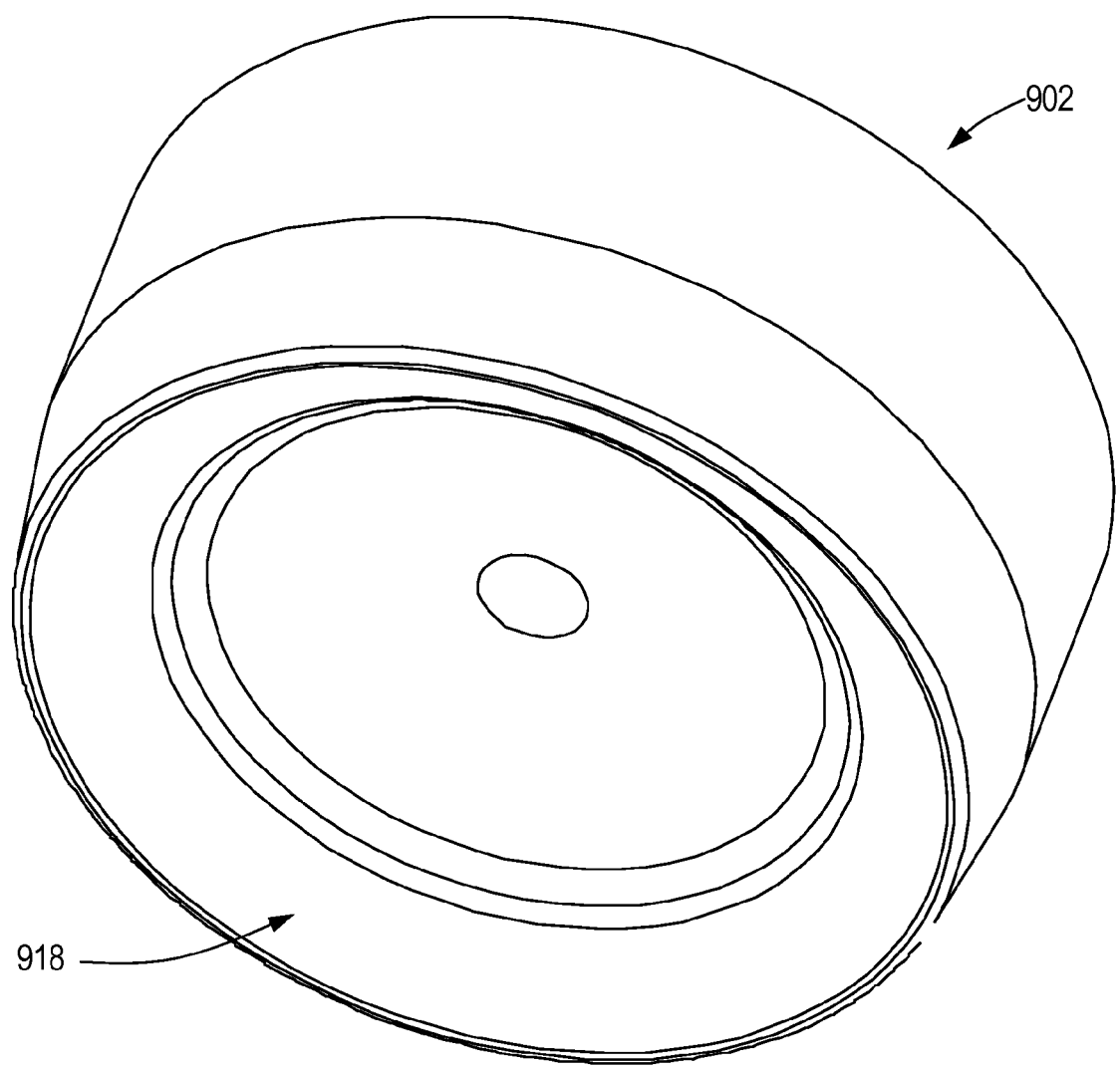
FIG. 28 is a perspective view of a rigid joint member used for comparison purposes.
Figure 29:
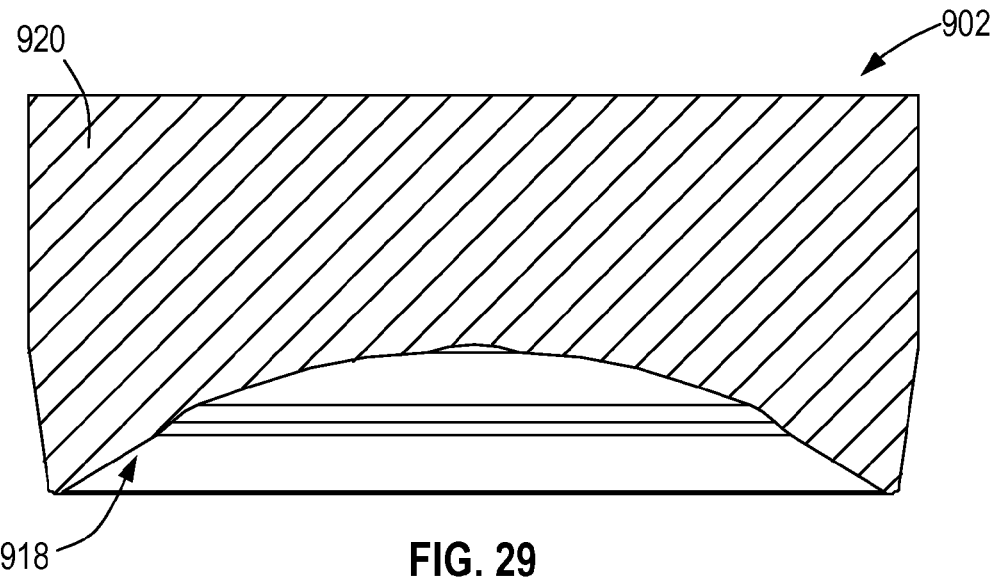
FIG. 29 is a cross-sectional view of the joint member shown in FIG. 28.
Figure 30:
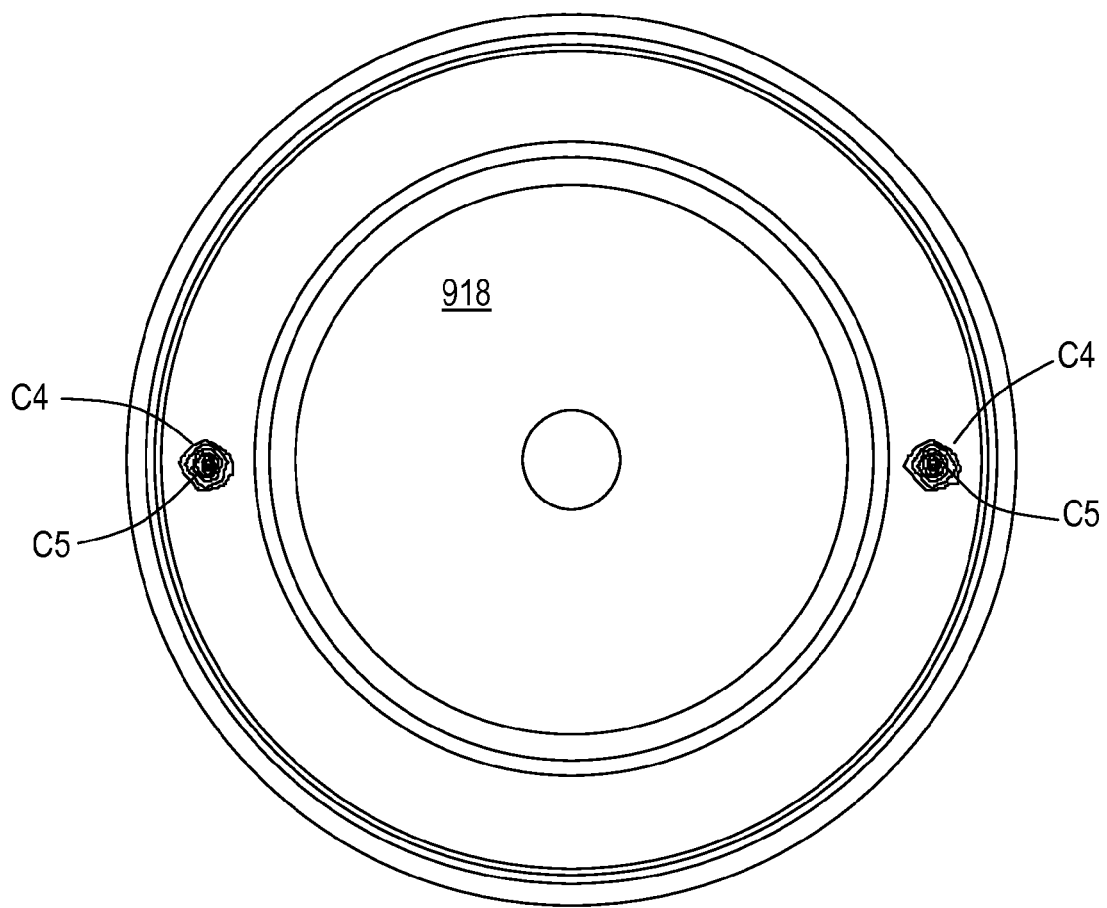
FIG. 30 is a contact stress plot of the joint member shown in FIG. 29.

For comparative purposes, FIGS. 28 and 29 depict a member 902 constructed according to prior art principles. The member 902 has a contact surface 918 with an identical profile and dimensions of the first contact surface 118 of the first member 102. However, consistent with the prior art, the member 902 has a massive body 920 behind the entire contact surface 918, rendering the entire member 902 substantially rigid. FIG. 30 graphically illustrates the expected contact stresses in the contact surface 918 as determined by analytical methods, when the member 902 is assembled and placed in contact with the second member 104, using the same applied load as depicted in FIG. 27. Because of the rigidity of the member 902, a "bridging" effect is present wherein contact between the contact surfaces (one of which is circular in plan view, and the other of which is elliptical) effectively occurs at only two points, located at approximately the three o'clock and nine o'clock positions. A first contour line "C4" shows two discrete areas where the lowest level of contract stress is present. These lines are not contiguous because there is no contact in the remaining area of the contact surfaces (for example at the six o'clock and twelve o'clock positions). Another contour line "C5" represents the areas of maximum contact stress. Analysis shows a peak contact stress having a magnitude of two to twenty times (or more) the peak contact stress of the inventive joint as shown in FIG. 27.

To achieve this controlled deflection, the flange 116 is thin enough to permit bending under working loads, but not so thin as to allow material yield or fatigue cracking. The deflection is opposed by the elasticity of the flange 116 in bending, as well as the hoop stresses in the flange 116. To achieve long life, the first member 102 is sized so that stresses in the flange 116 will be less than the endurance limit of the material, when a selected external load is applied. In this particular example, the joint 100 is intended for use between two spinal vertebrae, and the design average axial working load is in the range of about 0 N (0 lbs) to about 1300 N (300 lbs.). These design working loads are derived from FDA-referenced ASTM and ISO standards for spinal disc prostheses. In this example, the thickness of the flange 116, at a root 126 where it joins the body 106 (see FIG. 12) is about 0.04 mm (0.015 in.) to about 5.1 mm (0.200 in.), where the outside diameter of the flange 116 is about 6.4 mm (0.25 in.) to about 7.6 cm (3.0 in.).

Figure 17:
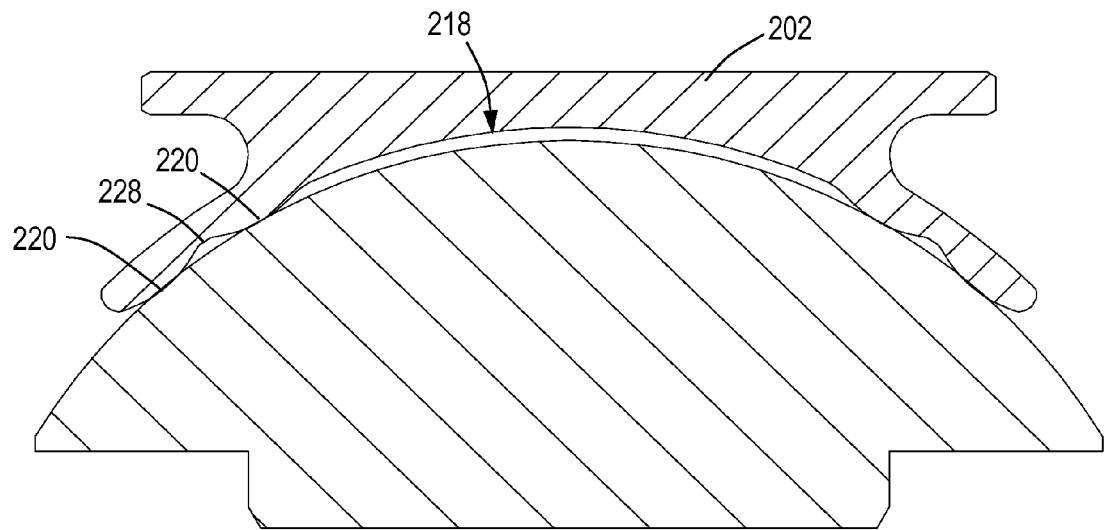
FIG. 17 is a cross-sectional view of another alternative joint member.

The joint members may include multiple rims. For example, FIG. 17 illustrates a joint member 202 where the first contact surface 218 includes two protruding rims 220, with a circumferential groove or relief area 228 therebetween. The presence of multiple rims increases the contact surface areas between the two joint members.

Figure 18:
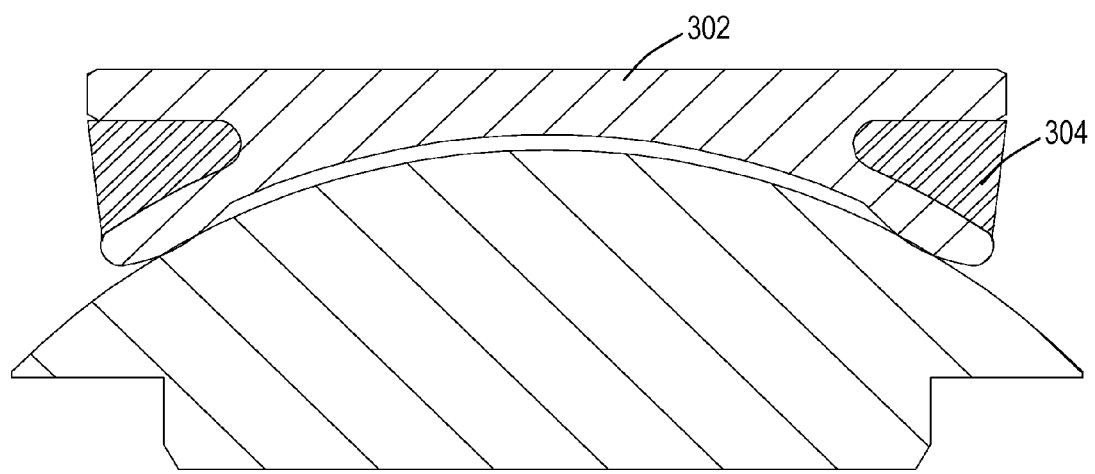
FIG. 18 is a cross-sectional view of another alternative joint member including a filler material.

If present, the circumferential gap between the flange and the base of the joint member may be filled with resilient nonmetallic material to provide damping and/or additional spring restoring force to the flange. FIG. 18 illustrates a joint member 302 with a filler 304 of this type. Examples of suitable resilient materials include polymers, natural or synthetic rubbers, and the like.

Figure 19:
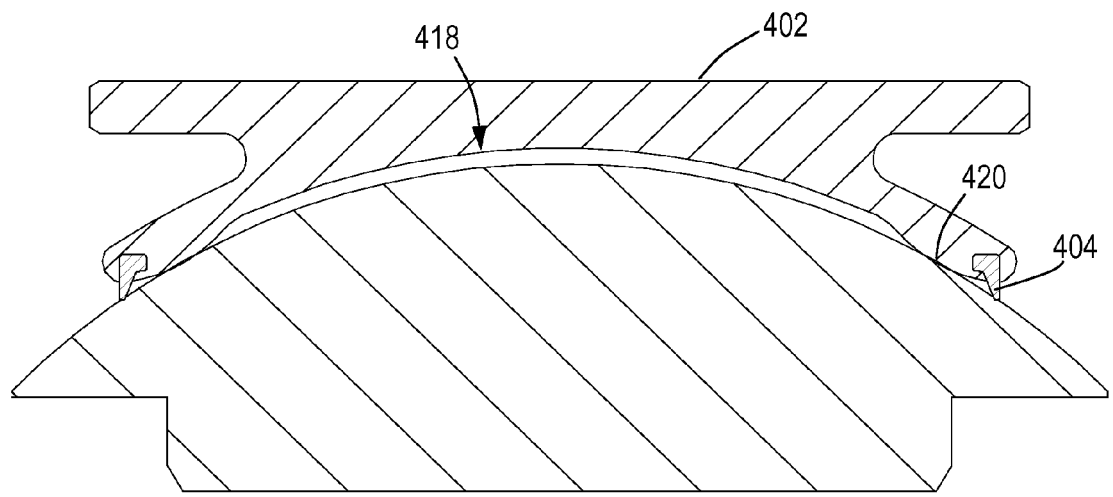
FIG. 19 is a cross-sectional view of another alternative joint member including a wiper seal.

As discussed above, the joint may incorporate a wiper seal. For example, FIG. 19 illustrates a joint member 402 with a resilient wiper seal 404 protruding from the rim 420 of the first contact surface 418. The wiper seal 404 keeps particles out of the contact area (seal void), while containing working fluid (natural or synthetic). The seal geometry is intended to be representative and a variety of seal characteristics may be employed; such as a single lip seal, a double or multiple lip seal. A pad or wiper seal may be made from a variety of material options. Different seal mounting options may be used, for example a lobe in shaped groove as shown in FIG. 18, a retaining ring or clamp, adhesion substance. The seal may also be incorporated into the contact face of the interface zone.

Figure 20:
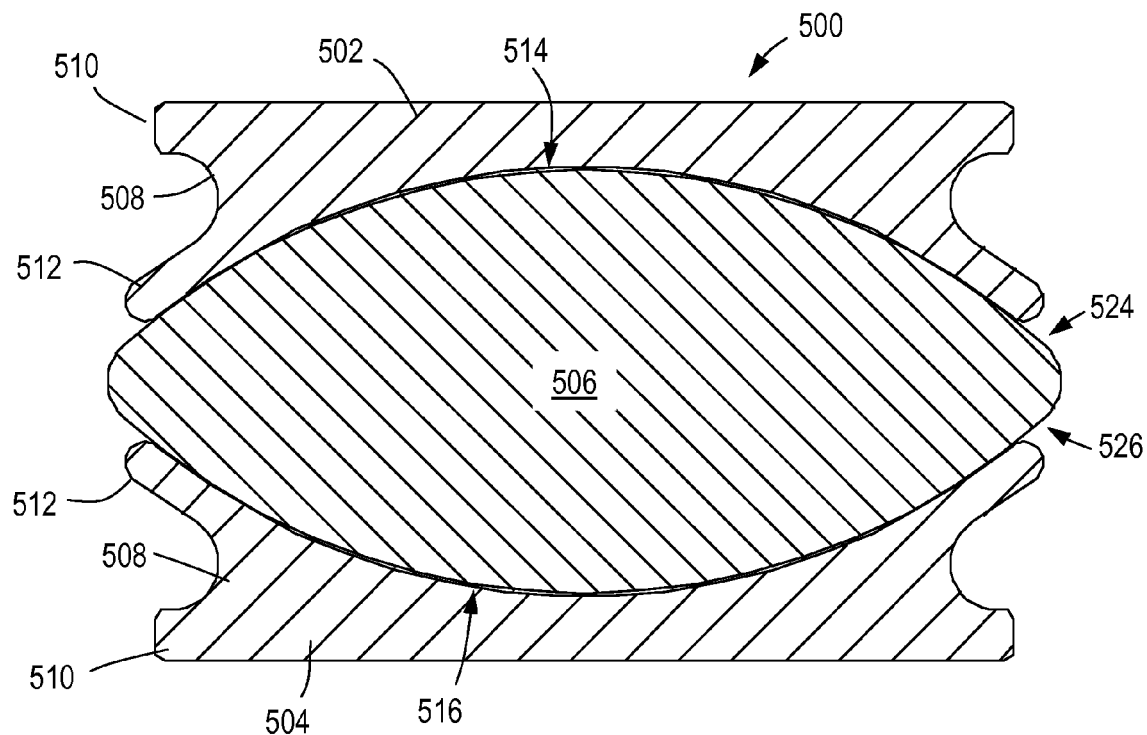
FIG. 20 is a cross-sectional view of another alternative prosthetic joint.

The joint construction described above can be extended into a three-part configuration. For example, FIG. 20 illustrates a prosthetic joint 500 having first, second, and third members 502, 504, and 506. The first and second members 502 and 504 are similar in construction to the first member 102 described above, and each includes a body 508, an optional disk-like base 510, and a flange 512. The flanges 512 define wear-resistant concave first and second contact surfaces 514 and 516, each of which includes a protruding peripheral rim, and a recessed central portion as described above. The third member 506 has a double-convex shape defining opposed wear-resistant, convex third and fourth contact surfaces 524 and 526. The first and second 514 and 516 bear against the third and fourth contact surfaces 524 and 526, respectively, so as to transfer axial (i.e. compression) and lateral loads between the first and second members 502 and 504 through the third member 506, while allowing pivoting motion between the members 502, 504, and 506. The first and second contact surfaces 514 and 516 are conformal to the third and fourth contact surfaces 524 and 526 as described in more detail above.

Figure 21:
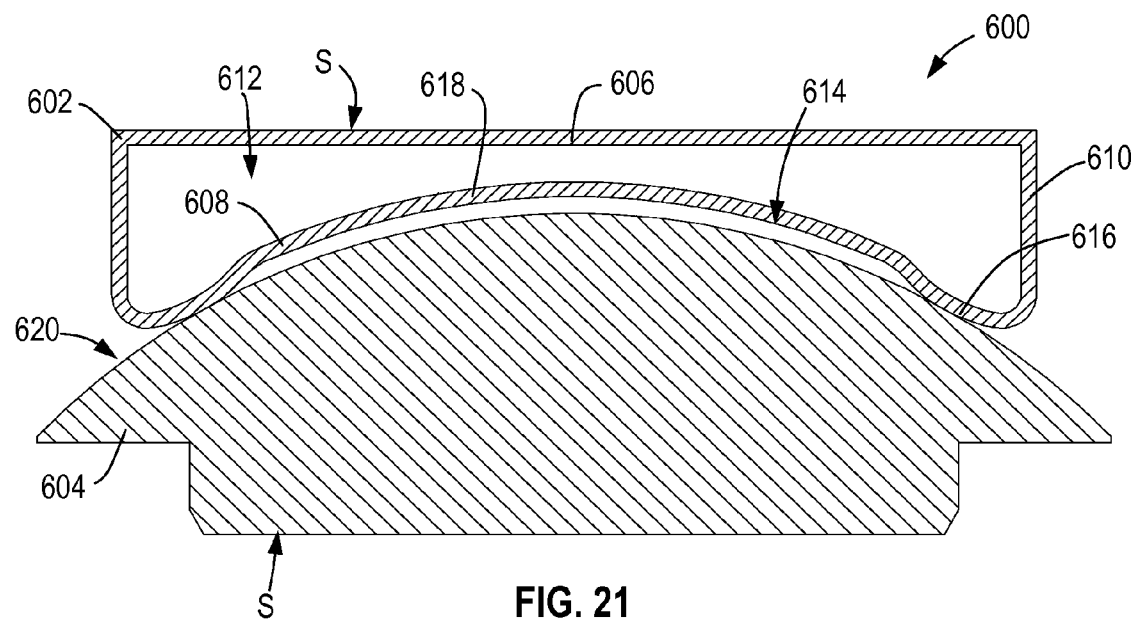
FIG. 21 is a cross-sectional view of a prosthetic joint constructed in accordance with another aspect of the present invention.

FIG. 21 illustrates an alternative prosthetic joint 600 comprising first and second members 602 and 604 constructed from rigid materials. Both of the members 602 and 604 are bone-implantable, meaning they include osseointegration surfaces, labeled "S", as described in more detail above.

The first member 602 is hollow and includes a disk-like base 606 and a cup 608, interconnected by a peripheral wall 610. An interior cavity 612 is defined between the base 606 and the cup 608. The cup 608 is constructed from a rigid material and defines a wear-resistant, concave first contact surface 614. The first contact surface 614 includes a protruding peripheral rim 616, and a recessed central portion 618, which may also be considered a "pocket" or a "relief". The rim 616 may have a conical or curved cross-sectional shape.

The second member 604 is constructed from a rigid material and has a wear-resistant, convex second contact surface 620. The first and second contact surfaces 614 and 616 bear directly against each other so as to transfer axial and laterals loads from one member to the other while allowing pivoting motion between the two members 602 and 604.

As described above with reference to the prosthetic joint 100, the cup 606 of the first member 602 is thin enough to permit bending under working loads, but not so thin as to allow material yield or fatigue cracking. The first contact surface 614 is thus conformable to the second contact surface 620 when the prosthetic joint 600 is placed under external load.

Figure 22:
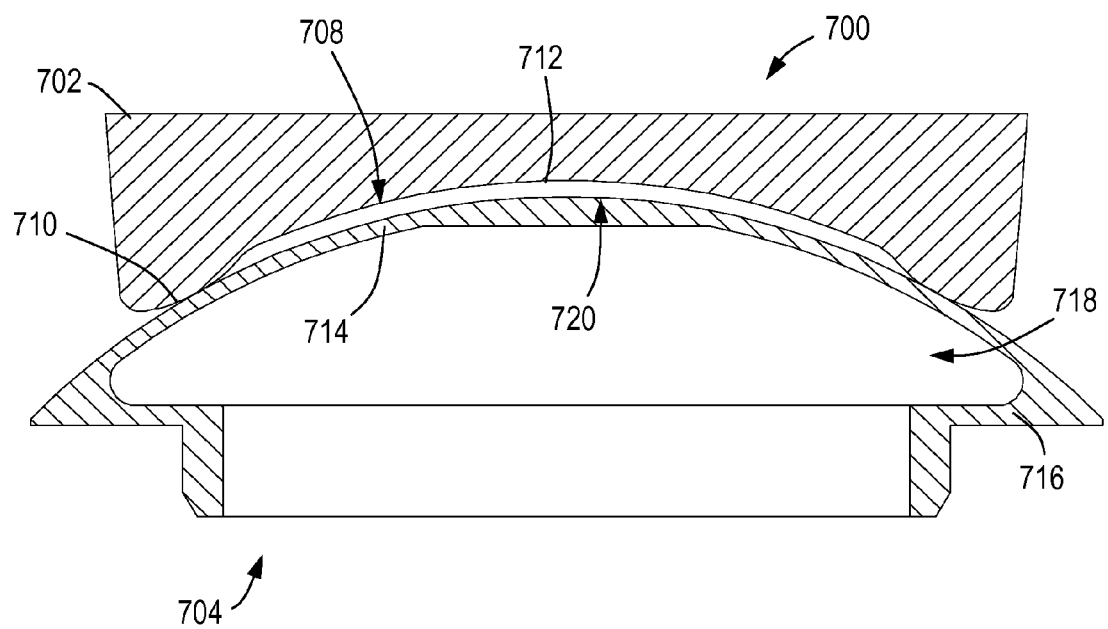
FIG. 22 is a cross-sectional view of a prosthetic joint constructed in accordance with yet another aspect of the present invention.

An inverted configuration of hollow members is also possible. For example, FIG. 22 illustrates a prosthetic joint 700 comprising first and second members 702 and 704, both constructed of rigid materials. The first member 702 is solid and includes a wear-resistant, concave first contact surface 708. The first contact surface 708 includes a protruding peripheral rim 710, and a recessed central portion 712, which may also be considered a "pocket" or a "relief".

The second member 704 is hollow and includes a dome 714 connected to a peripheral wall 716. An interior cavity 718 is defined behind the dome 714. The dome 714 defines a wear-resistant, convex second contact surface 720, which is shaped and sized enough to permit bending under working loads, but not so as to allow material yield or fatigue cracking. The second contact surface 720 is thus conformable to the first contact surface 708 when the prosthetic joint 700 is placed under external load.

The first and second contact surfaces 708 and 720 bear directly against each other so as to transfer axial and lateral loads from one member to the other while allowing pivoting motion between the two members 702 and 704.

Figure 23:
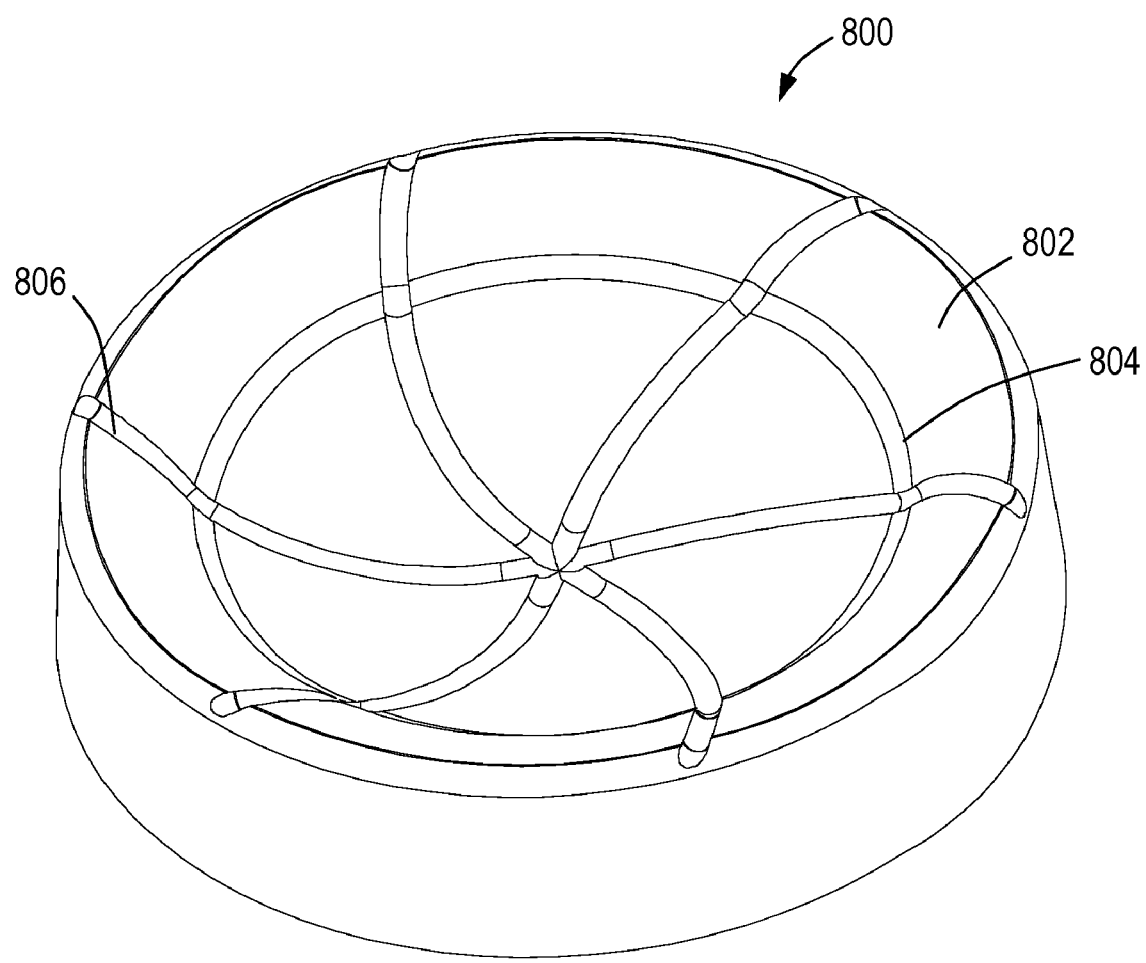
FIG. 23 is a perspective view of a joint member having a grooved surface.
Figure 24:
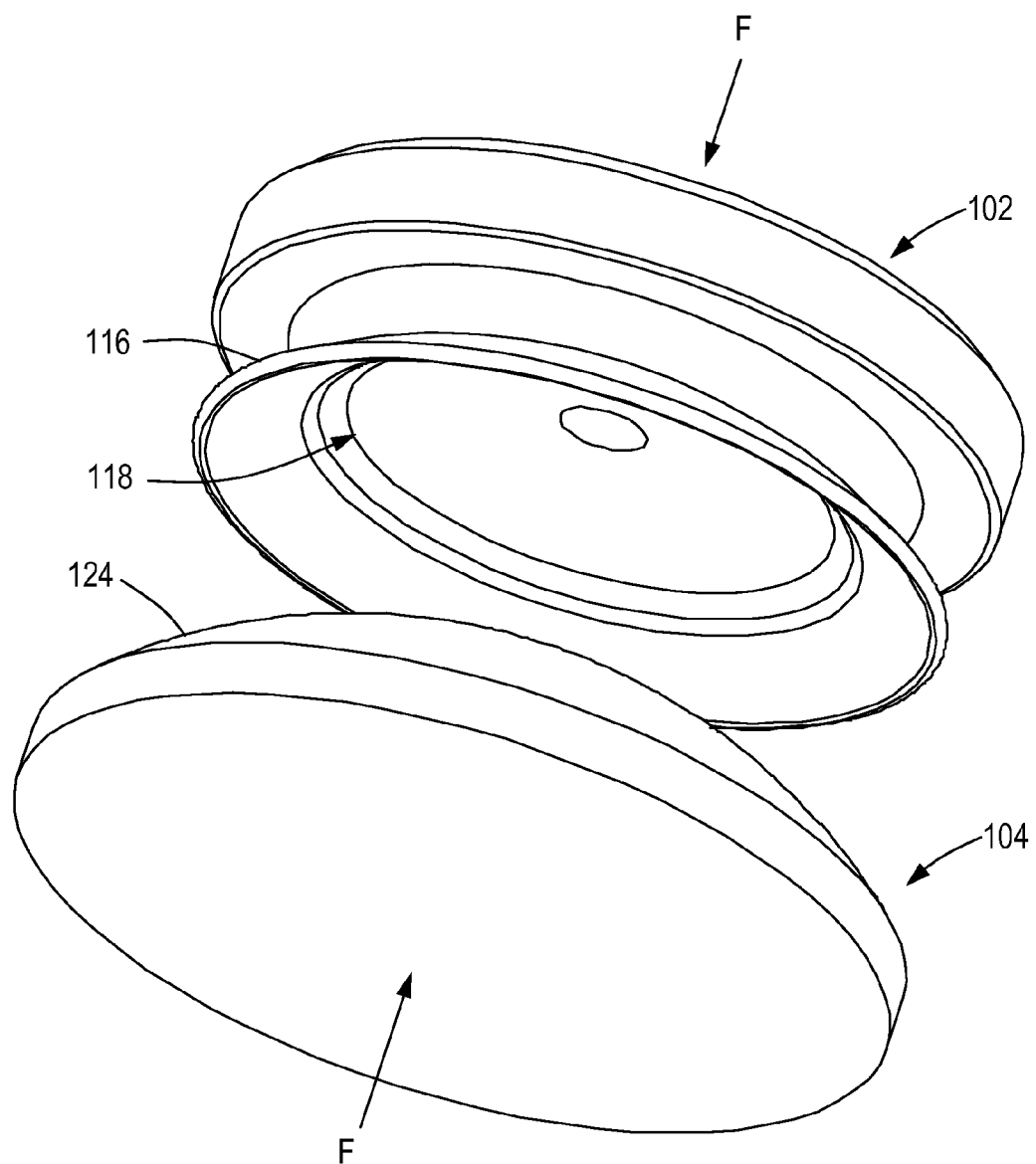
FIG. 24 is a exploded perspective view of two mating joint members.

Any of the contact surfaces described above may be provided with one or more grooves formed therein to facilitate flow of fluid or debris. For example, FIG. 23 illustrates a joint member 800 including a concave contact surface 802. The contact surface 802 includes a circular groove 804, and plurality of generally radially-extending grooves 806 which terminate at the center of the contact surface 802 and intersect the circular groove 804.

As noted above, known coatings such as titanium nitride, chrome plating, carbon thin films, and/or diamond-like carbon coatings may be used to impart wear resistance or augment the wear resistance of any of the first contact surfaces described above. To the same end, it may be desirable to surface treat either or both interfaces of any of the above-described implants or joints with a laser, shot peen, burnishing, or water shock process, to impart residual compressive stresses and reduce wear. The benefit could be as much from surface annealing and microstructure and microfracture elimination as smoothing itself.

The foregoing has described medical implants and prosthetic joints with wear-resistant properties and conformal geometries. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

What is claimed is:

1. A prosthetic joint having a central axis, comprising:
   (a) a bone-implantable first member comprising a rigid material and including a body having an annular flange extending outward from the body in a direction generally radial to the central axis at a first end of the body, where the flange and the body are parts of a monolithic whole, and where a thickness of the flange is substantially less than a thickness of the body, the first end of the body and the flange cooperatively defining a wear-resistant, concave first contact surface having a protruding rim and a recessed central portion; and
   (b) a bone-implantable second member comprising a rigid material with a wear-resistant, convex second contact surface;
   (c) where the first and second contact surfaces bear directly against each other so as to transfer axial and lateral loads from one of the members to the other, while allowing pivoting motion between the two members; and
   (d) wherein the flange is in contact with the second contact surface and is shaped and sized so as to deform elastically and permit the first contact surface to conform in an irregular shape to the second contact surface when the joint is placed under a predetermined load.

2. The prosthetic joint of claim 1 wherein the rim has a curved cross-sectional shape.

3. The prosthetic joint of claim 1, wherein the rim has a substantially conical surface.

4. The prosthetic joint of claim 3 wherein the rim has a free shape defining a first contact area with the second contact surface and a loaded shape defining a second contact area with the second contact surface which is substantially larger than the first contact area.

5. The prosthetic joint of claim 1 wherein:
   (a) the first member further includes a disk-like base disposed at a second end of the body opposite the first end, such that a circumferential gap is defined between the base and the flange; and
   (b) the circumferential gap filled with a resilient nonmetallic material.

6. The prosthetic joint of claim 1, wherein a resilient sealing lip protrudes from the rim and engages the second contact surface in a sealing relationship.

7. The prosthetic joint of claim 1 wherein the contact surfaces comprise a ceramic material, a metal, or a combination thereof.

8. The prosthetic joint of claim 1 wherein the first contact surface includes more than one protruding rim, with a circumferential relief area defined between adjacent rims.

9. The prosthetic joint of claim 1, wherein a thickness of the flange, at a root where it joins the neck, is about 0.04 mm to about 5.1 mm.

10. The prosthetic joint of claim 1, where the flange is sized so as to permit elastic deflection of the flange while limiting stresses in the flange to less than the endurance limit of the material from which the flange is constructed, when an external load in the range of about 0 to 300 lbs. is applied to the joint.

11. The prosthetic joint of claim 1, wherein the first contact surface has a pattern of grooves formed therein, comprising:
   (a) one or more circular grooves; and
   (b) one or more generally radially-aligned grooves which intersect the circular grooves.

* * * * *